United States Patent [19]
Kitada et al.

[11] Patent Number: 5,614,497
[45] Date of Patent: Mar. 25, 1997

[54] PEPTIDE, PRODUCTION AND USE THEREOF

[75] Inventors: Chieko Kitada, Sakai; Tetsuya Ohtaki, Tsukuba; Masahiko Fujino, Takarazuka, all of Japan

[73] Assignee: Takeda Chemical Industries, Ltd., Osaka, Japan

[21] Appl. No.: 992,131

[22] Filed: Dec. 17, 1992

[30] Foreign Application Priority Data

Dec. 27, 1991 [JP] Japan .................................. 3-346659
Jan. 27, 1992 [JP] Japan .................................. 4-012013
Oct. 8, 1992 [JP] Japan .................................. 4-269932

[51] Int. Cl.$^6$ ............................. A61K 38/00; C07K 7/00; C07K 7/06; C07K 5/10
[52] U.S. Cl. ............................. 514/17; 530/329; 530/330; 514/18
[58] Field of Search ................................. 530/329, 330; 514/17

[56] References Cited

U.S. PATENT DOCUMENTS

| | | | |
|---|---|---|---|
| 5,284,828 | 2/1994 | Hemmi et al. | 514/18 |
| 5,306,808 | 4/1994 | Wakimasu et al. | 530/326 |
| 5,352,659 | 10/1994 | Wakimasu et al. | 514/9 |
| 5,430,022 | 7/1995 | Hemmi et al. | 514/18 |
| 5,444,152 | 8/1995 | Ishikawa et al. | 530/331 |
| 5,470,833 | 11/1995 | Ishikawa et al. | 514/18 |
| 5,494,897 | 2/1996 | Ishikawa et al. | 514/18 |
| 5,496,928 | 3/1996 | Ishikawa et al. | 530/331 |

FOREIGN PATENT DOCUMENTS

| | | |
|---|---|---|
| 0460679A2 | 11/1991 | European Pat. Off. . |
| 0457195A2 | 11/1991 | European Pat. Off. . |
| 0457195 | 11/1991 | European Pat. Off. . |
| 0460679 | 12/1991 | European Pat. Off. . |
| 3130299 | 6/1991 | Japan . |

OTHER PUBLICATIONS

Stein et al. J. Of Medicinal Chemistry, vol. 37, No. 3, pp. 329–331.
Doherty, J. of Medicinal Chemistry, vol. 35, No. 9, May 1, 1992.
Eur. J. Pharmacol. 221:77 (1992), "Protective Effect of a Selective Endothelin Receptor Antagonist in Ischemic Acute Renal Failure in Rats".
J. Pharm. Exper. Therap., 270:728 (1994), "A New Endothelin Receptor Antagonist Shows Long–Lasting Inhibition of Endothelin–Mediated Blood Pressure Responses in Rats".
Ihara, et al, Life Sciences, vol. 50, pp. 247–255, 1992.
Fukuroda, Life Sciences, vol. 50, pp. 107–112, 1992.

Primary Examiner—Douglas W. Robinson
Assistant Examiner—S. G. Marshall
Attorney, Agent, or Firm—Foley & Lardner

[57] ABSTRACT

A peptide represented by the formula:

$$R_1-CO-N(R_2)-CH(R_3)-CO-NH-CH(R_4)-CO-N(R_5)-CH(R_6)-(CH_2)_n-CO-NH-(CH_2)_m-CO-X$$

[I]

(with the $R_2,R_3$ carbon in L configuration and the $R_4$ carbon in D configuration)

wherein $R_1$ represents an oil-soluble group; $R_2$ and $R_5$ represent a hydrogen atom or a lower alkyl group; $R_3$ represents an aliphatic group which may have O or S; $R_4$ represents a heterocyclic-substituted lower alkyl group; $R_6$ represents a hydrogen atom, a lower alkyl group or an aromatic cyclic group; X represents a group having an aromatic ring; n represents an integer of 0 or more and m represents an integer of 2 or more, or a salt thereof exhibits a marked endothelin receptor-antagonistic action, and the peptide [I] is pharmaceutically useful as a therapeutic agent for hypertension, cardiovascular disease and renal disease, for instance.

39 Claims, No Drawings

PEPTIDE, PRODUCTION AND USE THEREOF

The present invention relates to a new peptide, exhibiting endothelin receptor antagonistic action, which is pharmaceutically useful as a therapeutic agent for hypertension, a therapeutic agent for cerebrovascular disease, a therapeutic agent for renal disease, and a therapeutic agent for asthma; a method of production thereof and a use thereof.

Endothelin (ET), is a casoconstricting peptide comprising 21 amino acids, isolated from swine arterial endothelial culture supernatant and structurally determined by Yanagisawa et al. [Yanagisawa et al.: Nature, Vol. 332, pp. 411–415, 1988]. Endothelin was later found to exhibit various actions, and endothelin antibodies as endothelin antagonists have proven effective in the treatment of myocardial infarction, renal failure and other diseases. Since endothelin is present in live bodies and exhibits vasoconstricting action, it is expected to be an endogenous factor involved in the regulation of the circulatory system, and may be associated with hypertension, cardiovascular diseases such as myocardial infarction, and renal diseases such as acute renal failure. Since it also exhibits bronchial smooth muscle constricting action, it may be associated with asthma.

Recently, we have known endothelin antagonists described in (1) Japanese Patent Publication Nos. 130299/1991, (2) EP-A-457,195, (3) EP-A-460,679 and so on. As examples, the above (1), (2) and (3) describes respectively Boc-Leu-D-Trp(For)-D-Glu(OBzl)-Ala-OPac (1), Boc-L-Leu-D-Trp($CH_3$)-D-Pya-OH (2), Boc-Ile-D-Trp-β-Ala-OH (3), and so on.

These peptides, however, have defects which their endothelin antagonist activities are low. Then these peptide have not been used practically now.

If an excellent endothelin receptor antagonist is obtained, it will help clarify the action mechanism of endothelin, and will also offer a useful therapeutic agent for the above diseases. Accordingly, the object of the present invention is to provide a new compound having such an excellent effect.

The present inventors have studied intensively to solve the above problems. As a result, the inventors have succeeded in preparing a novel and relatively low molecular weight peptide which is different from the above (1), (2), (3) and have found that the peptide has an unexpectedly excellent receptor-antagonistic activity. According to further investigation, the inventors have attained the present invention.

Accordingly, the present invention relates to a peptide represented by the formula [I]:

Throughout in the specification, the compound [I] or peptide [I] may include the compound or peptide itself and the salt thereof.

Abbreviations for amino acids, peptides and others used in the present specification are based on abbreviations specified by the IUPAC-IUB Commission on Biochemical Nomenclature or abbreviations in common use in relevant fields. Some examples are given below.

| | |
|---|---|
| Ala | Alanine |
| Gly | Glycine |
| Val | Valine |
| Nva | Norvaline |
| Leu | Leucine |
| Ile | Isoleucine |
| Nle | Norleucine |
| Met | Methionine |
| Trp | Tryptophan |
| Tyr | Tyrosine |
| Phe | Phenylalanine |
| Glu | Glutamic acid |
| Asp | Aspartic acid |
| Gln | Glutamine |
| Asn | Asparagine |
| His | Histidine |
| Cys | Cysteine |
| Cha | Cyclohexylalanine |
| Phg | Phenylglycine |
| βAla | β-Alanine (β-Aminopropionic acid) |
| GABA | γ-aminobutyric acid |
| Aib | 2-aminoisobutyric acid |
| εAhx | ε-aminocaproic acid |
| (m-F)Tyr | m-fluorotyrosine |
| (p-F)Phe | p-fluorophenylalanine |
| Trp(Me) | $N^{in}$-methyltryptophan |
| Trp($CH_2OH$) | $N^{in}$-hydroxymethyltryptophan |
| Trp(CHO) | $N^{in}$-formyltryptophan |
| Pya(2) | 2-pyridylalanine |
| Pya(3) | 3-pyridylalanine |
| (I)Tyr | 3-Iodo-tyrosine |
| Thg(2) | 2-thienyl-glycine |
| Thg(3) | 3-thienyl-glycine |
| Thi | 2-thienyl-alanine |

The substituents, protective groups and reagents often used in the present specification and claims are symbolized as follows:

| | |
|---|---|
| Ph | Phenyl |
| Boc | tert-butoxycarbonyl |
| Bzl | Benzyl |
| HONB | N-hydroxy-5-norbornene-2,3-dicarboxyimide |
| DCC | N,N'-dicyclohexylcarbodiimide |
| DCHA | N,N'-dicyclohexylamine |
| WSCD | 1-ethyl-3-(3-dimethylaminopropyl)carbodiimide |
| HOBt | N-hydroxybenzotriazole |
| TosOH | p-toluenesulfonic acid |
| OPac | Phenacyl ester |
| Ind | 1-carboxyindan-2-yl |
| Iqu | 3-carboxy-1,2,3,4-tetrahydroisoquinolin-2-yl |
| Dba | 10,11-dihydro-5H-dibenz(b,f)azepin-5-yl |
| Pym | Pyrimidyl |
| Pip | Piperazyl |

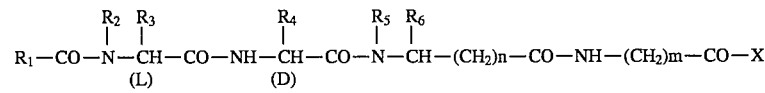

wherein $R_1$ represents an oil-soluble group; $R_2$ and $R_5$ independently represent a hydrogen atom or a lower alkyl group; $R_3$ represents an aliphatic group which may have an oxygen atom or a sulfur atom; $R_4$ represents a heterocyclic-substituted lower alkyl group which may be substituted; $R_6$ represents a hydrogen atom, a lower alkyl group which may be substituted or an aromatic cyclic group which may be substituted; X represents a group having an aromatic ring; n represents an integer of 0 or more; m represents an integer of 2 or more, or a salt thereof, a method of production thereof and a pharmaceutical composition containing peptide [I] or a pharmacologically acceptable salt thereof.

For example, in the present specification, Glu-OBzl represents a benzyl ester at the 1-carboxyl group of Glu; Glu(OBzl) represents a benzyl ester at the 5-carboxyl group of Glu; Asp-NHCH$_2$CH$_3$ represents an ethylamide at the 1-carboxyl group of Asp; Asp(NHCH$_2$CH$_3$) represents an ethylamide at the 4-carboxyl group of Asp.

With respect to the above formula [I], $R_1$ represents an oil-soluble group. The oil-soluble group may be any group, as long as the oil solubility of a compound is increased by binding it therewith. Examples of such oil-soluble groups include alkyl groups, cycloalkyl groups, alkoxy groups, aromatic cyclic groups and amino groups having a substituent, which groups may be further substituted.

The alkyl group for $R_1$ is preferably a straight or branched alkyl group having 1 to 10 carbon atoms, including methyl, ethyl, n-propyl, isopropyl, n-butyl, isobutyl, sec-butyl, tert-butyl, n-pentyl, isoamyl, tert-amyl, neopentyl, n-hexyl, n-heptyl, n-octyl, n-nonyl and n-decyl. Lower alkyl groups having 1 to 6 carbon atoms (e.g., methyl, ethyl, n-propyl, isopropyl, n-butyl, isobutyl, sec-butyl, tert-butyl, n-pentyl, isoamyl, tert-amyl, neopentyl, n-hexyl) are particularly preferable.

These alkyl groups may be substituted. Example substituents include $C_{3-8}$ cycloalkyls (e.g., cyclopentyl, cyclohexyl), halogens (e.g., fluorine, chlorine, bromine, iodine), $C_{1-6}$ alkoxys (e.g., methoxy, ethoxy, n-propoxy, isopropoxy, n-butoxy, tert-butoxy), $C_{1-6}$ alkylthios (e.g., methylthio, ethylthio, n-propylthio, isopropylthio, n-butylthio, tert-butylthio), $C_{1-6}$ alkoxycarbonyls (e.g., methoxycarbonyl, ethoxycarbonyl isopropoxycarbonyl, tert-butoxycarbonyl), aromatic cyclic groups (e.g., $C_{6-12}$ aromatic hydrocarbon groups which may be substituted by a halogen, hydroxy, $C_{1-3}$ alkoxy, $C_{1-3}$ alkyl group, and so on such as phenyl, fluorophenyl, chlorophenyl, bromophenyl, hydroxyphenyl, methoxyphenyl, methylphenyl, 1-naphthyl and 2-naphthyl, and 5- to 10-membered aromatic heterocyclic groups which contain 1 to 4 hetero atoms such as O, S, N and others such as furyl, thienyl, thiazolyl, indolyl, pyridyl, pyranyl, imidazolyl, pyrimidyl and quinolyl). The number of substituents of these alkyl groups is preferably 1 to 3.

The cycloalkyl group for $R_1$ is preferably a cycloalkyl group having 3 to 10 carbon atoms, including cyclopropyl, cyclobutyl, cyclopentyl, cyclohexyl, cycloheptyl, cyclooctyl, adamantyl, bornyl and norbornyl. These cycloalkyl groups may be substituted. Example substituents include $C_{1-6}$ alkyls (e.g., methyl, ethyl, n-propyl, n-butyl), halogens (e.g., fluorine, chlorine, bromine, iodine), $C_{1-6}$ alkoxys (e.g., methoxy, ethoxy, n-propoxy, isopropoxy, n-butoxy, tert-butoxy), $C_{1-6}$ alkylthios (e.g., methylthio, ethylthio, n-propylthio, isopropylthio, n-butylthio, tert-butylthio) and $C_{1-6}$ alkoxycarbonyls (e.g., methoxycarbonyl, ethoxycarbonyl, isopropoxycarbonyl, tert-butoxycarbonyl). The number of substituents of these cycloalkyl groups is preferably 1 to 3. These cycloalkyl groups as condensed with another ring such as a benzen ring (e.g., indan-1-yl, indan-2-yl, 1,2,3,4-tetrahydronaphthalene-1-yl, 1,2,3,4-tetrahydronaphthalene-2-yl) are also included.

The alkoxy group for $R_1$ is preferably a straight or branched alkoxy group having 1 to 8 carbon atoms, including methoxy, ethoxy, n-propoxy, isopropoxy, n-butoxy, isobutoxy, sec-butoxy, tert-butoxy, n-pentyloxy, isoamyloxy, tert-amyloxy, neopentyloxy, n-hexyloxy, n-heptyloxy and n-octyloxy. These alkoxy groups may be substituted. Example substituents include $C_{3-8}$ cycloalkyl groups (e.g., cyclopentyl, cyclohexyl), $C_{1-6}$ alkoxys (e.g., methoxy, ethoxy, n-propoxy, isopropoxy, n-butoxy, tert-butoxy) and $C_{1-6}$ alkoxycarbonyls (e.g., methoxycarbonyl, ethoxycarbonyl, isopropoxycarbonyl, tert-butoxycarbonyl). The number of substituents of these alkoxy groups is preferably 1 to 3. The alkyl group or alkoxy group for $R_1$ is preferably branched rather than straight.

The aromatic cyclic group for $R_1$ may be an aromatic hydrocarbon group or an aromatic heterocyclic group. Example aromatic hydrocarbon groups include those having 6 to 15 carbon atoms such as phenyl, $\alpha$-naphtyl and so on. These aromatic hydrocarbon groups maybe substituted by 1 to 3 substituents selected from the group consisting of halogen atoms (ex. flurine, chlorine, bromine), hydroxy group, $C_{1-6}$ alkyl group (ex. methyl, ethyl), $C_{1-6}$ alkoxy group (ex. methoxy, ethoxy), carbonyl group, $C_{1-6}$ alkylcarbonyl (ex. formyl, acetyl), $C_{1-6}$ alkoxy carbonyl (ex. methoxycarbonyl) and so on. Examples of aromatic hydrocarbon groups which may be substituted are preferably phenyl, 4-fluorophenyl, 4-chlorophenyl, 4-bromophenyl, 4-hydroxyphenyl, 4-methoxyphenyl, 4-methylphenyl, 1-naphthyl, 2-naphthyl. Example aromatic heterocyclic groups include 5- or 6-membered groups having 1 to 4 hetero atoms of O, S, N and others (e.g., 2-furyl, 3-furyl, 2-thienyl, 3-thienyl, thiazol-4-yl, 2-pyridyl, 3-pyridyl, 4-pyridyl, 2-pyranyl) and these groups as condensed with other aromatic rings such as a benzen ring (e.g., indol-3-yl, N-methylindol-3-yl, 2-quinolyl, quinoxalin-2-yl). These aromatic heterocyclic groups may have 1 to 3 substituents which are same as those of the above mentioned aromatic hydrocarbon groups.

The amino group substituted for $R_1$ is preferably a mono-substituted amino group ($R_7$NH-) or a di-substituted amino group ($R_8R_9$N-), wherein $R_7$, $R_8$ and $R_9$ independently represent groups capable of providing oil solubility for the substituted amino group. Examples of such groups for $R_7$, $R_8$ and $R_9$ include alkyl groups having 4 or more carbon atoms and cycloalkyl groups or aromatic cyclic groups having 5 or more carbon atoms. The alkyl group having 4 or more carbon atoms is preferably an alkyl gropu having 4 to 10 carbon atoms, including n-butyl, isobutyl, sec-butyl, tert-butyl, n-pentyl, isoamyl, tert-amyl, neopentyl, n-hexyl, n-heptyl, n-octyl, n-nonyl and n-decyl. The cycloalkyl group having 5 or more carbon atoms is preferably a cycloalkyl group having 5 to 10 carbon atoms, including cyclopentyl, cyclohexyl, cycloheptyl, cyclooctyl, adamantyl, bornyl and norbornyl. Example aromatic cyclic groups for $R_7$, $R_8$ and $R_9$ include $C_{6-12}$ aromatic hydrocarbons such as phenyl, 1-naphthyl and 2-naphthyl, 5- to 10-membered aromatic heterocyclic groups which contain 1 to 4 hetero atoms of O, S, N and others (e.g. furyl, thienyl, thiazolyl, pyridyl and pyranyl), and these aromatic groups as condensed with another aromatic ring such as a benzen ring, such as indolyl, quinolyl and quinoxalyl. These alkyl groups, cycloalkyl groups and aromatic cyclic groups may have 1 to 3 additional substituents. Example substituents for the alkyl group include $C_{3-8}$ cycloalkyls (e.g., cyclopentyl, cyclohexyl), $C_{1-6}$ alkoxys (e.g., methoxy, ethoxy, n-propoxy, isopropoxy, n-butoxy, tert-butoxy), $C_{1-6}$ alkylthios (e.g., methylthio, ethylthio, n-propylthio, isopropylthio, n-butylthio, tert-butylthio), hydroxyl, carboxyl, $C_{1-6}$ alkylcarbonyls (e.g., formyl, acetyl), aromatic cyclic groups (e.g., $C_{6-12}$ aromatic hydrocarbon groups which may be substituted by a halogen atom, hydroxy group, $C_{1-3}$ alkoxy group or $C_{1-3}$ alkyl group such as phenyl, fluorophenyl, chlorophenyl, bromophenyl, hydroxyphenyl, methoxyphenyl, methylphenyl, 1-naphthyl and 2-naphthyl, and 5- to 10- membered aromatic heterocyclic groups which contain 1 to 4 hetero atoms of O, S, N and others such as furyl, thienyl, thiazolyl, indolyl, pyridyl, pyranyl, imidazolyl, pyrimidyl and quinolyl). Example of the substituents for the cycloalkyl group include $C_{1-6}$ alkyls (e.g., methyl, ethyl, n-propyl, n-butyl), $C_{1-6}$ alkoxys (e.g., methoxy, ethoxy, n-propoxy, isopropoxy, n-butoxy, tert-butoxy), $C_{1-6}$ alkylthios (e.g., methylthio, ethylthio, n-propylthio, isopropylthio, n-butylthio, tert-butylthio), hydroxy, carboxyl, $C_{1-6}$ alkylcarbonyls (e.g., formyl, acetyl) and so on. Example substituents for the aromatic cyclic group on carbon atoms include $C_{1-6}$ alkyls (e.g., methyl, ethyl, n-propyl, n-butyl), $C_{1-6}$ alkoxys (e.g., methoxy, ethoxy, n-propoxy, n-butoxy), hydroxyl, carboxyl, $C_{1-6}$ alkyl (e.g., formyl, acetyl) and so on. Example substituents for the aromatic cyclic group on nitrogen atoms include $C_{1-6}$ alkyls (e.g., methyl, ethyl, n-propyl, n-butyl). The di-substituted amino groups ($R_8R_9N$-) also include those wherein $R_8$ and $R_9$ bind together to form a ring. Examples of the ring which $R_8$ and $R_9$ bind together to form include a 5- to 9- membered nitrogen-containing heterocyclic ring which may have 1 or 2 hetero atoms such as oxygen atom and sulfur atom. Examples of the nitrogen-containing heterocyclic ring include pyrrolidinyl, piperidinyl, hexamethyleneiminyl, heptamethyleneiminyl, oxazolidinyl, morphonyl, thiazolidinyl, thiomorphonyl, imidazolidinyl, piperazinyl, pyrrolyl, 1,2-dihydropyridinyl, 1,4-dihydropyridinyl, 1,2,3,6-tetrahydropyridinyl, 2-oxazolidonyl, 2-thiazolidonyl, imidazolyl, 1,4,5,6-tetrahydropyrimidinyl, 2-3-dihydro-1H-indolyl, 1,2, 3,4-tetrahydroquinolinyl, 2,3,4,5-tetrahydro-1H-1-benzazepinyl, 2,3-dihydro-1H-isoindolyl, 1,2,3,4-tetrahydroisoquinolyl, 2,3,4,5-tetrahydro-1H-2-benzazepinyl, 2,3,4,5-tetrahydro-1H-3-benzazepinyl, 1,2,3,4,5,6-hexahydro-1-benzazocinyl, 1,2,3,4,5,6-hexahydro-2-benzazocinyl, 1,2,3,4,5,6-hexahydro-3-benzazocinyl, 2,3,4,5,6,7-hexahydro=1H-1-benzazonyl, 2,3,4,5,6,7-hexahydro-1H-2-benzazonyl, 2,3,4,5,6,7-hexahydro-1H-3-benzazonyl, 2,3,4, 5,6,7-hexahydro-1H-4-benzazonyl, β-carbolynyl, phenoxadinyl, phenothiadinyl, 3H-3-benzazepinyl, 3,4-dihydroquinolyl, benzimidanyl, 1,4-benzodiazepinyl, 10,11-dihydro-5H-dibenz (b,f) azepine-5-yl and so on. The preferable examples include a hexamethyleneiminyl, 10,11-dihydro-5H-dibenz (b,f) azepine-5-yl, morphonyl, piperidinyl, piperadinyl and so on.

These nitrogen-containing heterocyclic rings may have 1 to 3 substituents.

Examples of the substituents include a $C_{1-6}$ alkyl group (e.g. methyl, ethyl, n-propyl, isopropyl), a phenyl group, a halogen atom (e.g. fluoro, chlore, brome, iodo), a nitro group, a cyano group, a hydroxy group, a $C_{1-4}$ alkoxy group (e.g. methoxy, ethoxy, n-propoxy, n-butoxy, isopropoxy), a $C_{1-4}$ alkylthio group (e.g. methylthio, ethylthio, propylthio, isopropylthio), an amino group, a mono- or di-$C_{1-4}$ alkylamino group (e.g. methylamino, ethylamino, propylamino, dimethylamino, diethylamino), a $C_{1-4}$ alkylcarbonylamino group (e.g. formylamino, acetylamino, propyonylamino, butylylamino), a $C_{1-4}$ alkylsulfonylamino group (e.g. methylsulfonylamino, ethylsulfonylamino), a $C_{1-4}$ alkoxycarbonyl group (e.g. methoxycarbonyl, ethoxycarbonyl, propoxycarbonyl), a carboxyl group, a $C_{1-6}$ alkylcarbonyl group (e.g. formyl, methylcarbonyl, ethylcarbonyl, propylcarbonyl), a $C_{1-4}$ alkylcarbonyloxy group (e.g. acetyl, ethylcarbonyloxy), a 5- or 6- membered heterocyclic group having 1 to 4 hetero atoms such as O, S, N and others (e.g. pyridinyl, furyl, thiophenyl). More preferable mono-substituted amino groups ($R_7NH$-) include cyclohexylamino, phenylamino (anilino) and benzylamino. More preferable di-substituted amino groups ($R_8R_9N$-) include dicyclohexylamino, diphenylamino, hexamethyleneimino (homopiperidino), 10,11-dihydro-5H-dibenz(b,f)azepin-5-yl(Dba), morpholino, piperidino, methylpiperazino and 1-(2-pyrimidyl) piperazino.

With respect to formula [I], $R_2$ and $R_5$ independently represent a hydrogen atom or a lower alkyl group. The lower alkyl group is preferably a straight or branched alkyl group having 1 to 6 carbon atoms, including methyl, ethyl, n-propyl, isopropyl, n-butyl, isobutyl, sec-butyl, tert-butyl, n-pentyl, isoamyl, tert-amyl, neopentyl and n-hexyl. For $R_2$ and $R_5$, a hydrogen atom or $C_{1-3}$ alkyl group such as a methyl is particularly preferable.

With respect to formula [I], $R_3$ represents an aliphatic group which may have an oxygen atom or a sulfur atom. The aliphatic groups is preferably an alkyl group, a cycloalkyl group or a cycloalkylalkyl group. The methylene ($CH_2$) in these aliphatic groups at any position other than the α position may be substituted by an oxygen atom or a sulfur atom. The alkyl group is preferably a straight or branched alkyl group having 1 to 8 carbon atoms, including methyl, ethyl, n-propyl, isopropyl, n-butyl, isobutyl, sec-butyl, tert-butyl, n-pentyl, isoamyl, tert-amyl, neopentyl, n-hexyl, n-heptyl, n-octyl, methoxymethyl, ethoxymethyl, 2-methoxyethyl, 2-ethoxyethyl, 3-methoxypropyl, 3-ethoxypropyl, methylthiomethyl, ethylthiomethyl, 2-methylthioethyl, 2-ethylthioethyl, 3-methylthiopropyl and 3-ethylthiopropyl, with more preference given to alkyl groups having 1 to 6 carbon atoms (e.g., methyl, ethyl, n-propyl, isopropyl, n-butyl, isobutyl, sec-butyl, tert-butyl, n-pentyl, isoamyl, tert-amyl, neopentyl, n-hexyl). The cycloalkyl group is preferably a cycloalkyl group having 3 to 8 carbon atoms, including cyclopropyl, cyclobutyl, cyclopentyl, cyclohexyl, cycloheptyl, cyclooctyl, tetrahydrofuran-2-yl and tetrahydrothiophen-2-yl. The cycloalkylalkyl group is preferably a straight or branched alkyl group having 1 to 8 carbon atoms substituted by a cycloalkyl group having 3 to 8 carbon atoms, including cyclopentylmethyl, cyclohexylmethyl, 2-(cyclopentyl)ethyl, 2-(cyclohexyl)ethyl, cyclopentylthiomethyl and cyclohexylthiomethyl. $R_3$ is preferably a $C_{1-6}$ alkyl group, with greatest preference given to butyl groups (e.g., n-butyl, isobutyl, sec-butyl, tert-butyl). The carbon atom to which $R_3$ is bound is an asymmetric carbon; compound [I] of the present invention exhibits marked endothelin receptor-antagonistic action because its $R_3$ is of the L-configuration.

With respect to formula [I], $R_4$ represents a heterocyclic-substituted lower alkyl group which may be substituted.

The heterocyclic-substituted lower alkyl group is a lower alkyl group substituted by a heterocyclic group. Examples of the heterocyclic group include 5- or 6-membered heterocyclic groups having 1 to 4 hetero atoms of O, S, N and others (e.g., pyrrolyl, pyrrolinyl, pyrrolidinyl, imidazolyl, imidazolidinyl, piperidinyl, pyrazolyl, pyrazolidinyl, pyridinyl, pyrimidyl, pyradinyl, piperadinyl, pyridazinyl, triazolyl, tetrazolyl, dihydrotriadinyl, pyridyl, oxazolyl, isoxazolyl, oxadiazolyl, morpholinyl, furyl, thienyl, thiazolyl, isothiazolyl, thiazolinyl, thiadiazolyl, triazolidinyl) and these groups as condensed with other rings such as benzen ring (e.g., indolyl, isoindolyl, indolidinyl, benzimidazolyl, quinolyl, isoquinolyl, indazolyl, benzotriazolyl, tetrazolopyridyl, tetrazolopyridadinyl, benzoxazolyl, benzoxadiazolyl, benzothiazolyl, benzothiadiazolyl). These heterocyclic groups may have 1 to 3 substituents. Examples substituents for the heterocyclic group on carbon atoms include $C_{1-6}$ alkyls (e.g., methyl, ethyl, n-propyl, n-butyl), halogens (e.g., fluorine, chlorine, bromine, iodine), hydroxyl, carboxyl, $C_{1-6}$ alkoxys (e.g., methoxy, ethoxy, n-propoxy, n-butoxy), $C_{1-6}$ alkylcarbonyls (e.g., formyl, acetyl). Example substituents on nitrogen atoms include $C_{1-6}$ alkyls (e.g., methyl, ethyl, n-propyl, n-butyl), $C_{1-6}$ alkylcarbonyl (e.g., formyl, acetyl) and hydroxy-$C_{1-6}$ alkyls (e.g., hydroxymethyl, 2-hydroxyethyl). The lower alkyl group is preferably a straight or branched alkyl group having 1 to 6 carbon atoms, including methyl, ethyl, n-propyl, isopropyl, n-butyl, isobutyl, sec-butyl, tert-butyl, n-pentyl, isoamyl, tert-amyl, neopentyl and n-hexyl. Thus, the heterocyclic-substituted lower alkyl group is preferably a heterocyclic-substituted $C_{1-6}$ alkyl group. Examples of such alkyl groups include 2-pyridyl-$C_{1-6}$ alkyls (e.g., 2-pyridilmethyl, 2-(2-pyridyl)ethyl), 3-pyridyl-$C_{1-6}$ alkyls (e.g., 3-pyridilmethyl, 2-(3-pyridyl)ethyl), 4-pyridyl-$C_{1-6}$ alkyls (e.g., 4-pyridilmethyl, 2-(4-pyridyl)ethyl), imidazol-2-yl-$C_{1-6}$ alkyls (e.g., imidazol-2-ylmethyl, 2-(imidazol-2-yl)ethyl), imidazol-4-yl-$C_{1-6}$ alkyls (e.g., imidazol-4-ylmethyl, 2-(imidazol-4-yl)ethyl), indol-3-yl-$C_{1-6}$ alkyls (e.g., indol-3-ylmethyl, 2-(indol-3-yl)ethyl), N-methylindol-3-yl-$C_{1-6}$ alkyls (e.g., N-methylindol-3-ylmethyl, 2-(N-methylindol-3-yl)ethyl), N-ethylindol-3-yl-$C_{1-6}$ alkyls (e.g., N-ethylindol-3-ylmethyl, 2-(N-ethylindol-3-yl)ethyl), N-hydroxymethylindol-3-yl-$C_{1-6}$ alkyls (e.g., N-hydroxymethylindol-3-ylmethyl, 2-(N-hydroxymethylindol-3-yl)ethyl), N-formylindol-3-yl-$C_{1-6}$ alkyls (e.g., N-formylindol-3-ylmethyl, 2-(N-formylindol-3-yl)ethyl), thiazol-4-yl-$C_{1-6}$ alkyls (e.g., thiazol-4-ylmethyl, 2-(thiazol-4-yl)ethyl), and 5-fluoroindol-3-yl-$C_{1-6}$ alkyls (e.g., 5-fluoroindol-3-ylmethyl, 2-(5-fluoroindol-3-yl)ethyl). $R_4$ is preferably an indol-3-yl-$C_{1-6}$ alkyl which may be substituted, with greatest preference given to indol-3-ylmethyl, N-methylindol-3-ylmethyl, N-hydroxymethylindol-3-ylmethyl etc.

The carbon atom to which $R_4$ is bound is an asymmetric carbon; compound [I] of the present invention exhibits marked endothelin receptor-antagonistic action because its $R_4$ is of the D-configuration.

With respect to formula [I], X represents a group having an aromatic ring. Specifically, such groups include groups resulting from elimination of one hydrogen atom from the α-amino group of α-amino acids having at least one aromatic cyclic group, and alkylamino groups substituted by an aromatic cyclic group. In other words, it is preferable that CO and X be bound via an amide bond. The aromatic cyclic group is exemplified by aromatic hydrocarbon groups and aromatic heterocyclic groups which may be substituted. Preferable aromatic hydrocarbon groups which may be substituted include $C_{6-15}$ aromatic hydrocarbon groups such as phenyl, α-naphtyl and so on. These aromatic hydrocarbon groups may be substituted by 1 to 3 substituents selected from the group consisting of halogen atoms (ex. fluorine chlorine, bromine), hydroxy group, $C_{1-6}$ alkyl group (ex. methyl, ethyl), $C_{1-6}$ alkoxy group (ex. methoxy, ethoxy), carboxyl group, $C_{1-6}$ alkylcarbonyl (ex. formyl, acetyl), $C_{1-6}$ alkoxycarbonyl (ex. methoxy carbonyl) and so on. Examples of aromatic hydrocarbon groups which may be substituted are preferably phenyl, 4-fluorophenyl, 4-chlorophenyl, 4-bromophenyl, 4-hydroxyphenyl, 4-methoxyphenyl, 4-methoylphenyl, 1-naphthyl, 2-naphthyl. Preferable aromatic heterocyclic groups which may be substituted include 5- or 6-membered aromatic heterocyclic groups having 1 to 4 hetero atoms of O, S, N and others and these groups as condensed with other aromatic rings such as a benzen ring (e.g., 2-furyl, 3-furyl, 2-thienyl, 3-thienyl, thiazol-4-yl, 2-pyridyl, 3-pyridyl, 4-pyridyl, 2-pyranyl, indol-3-yl, N-methylindol-3-yl, 2-quinolyl, quinoxalin-2-yl). These aromatic heterocyclic groups may have 1 to 3 substituents which are same as those of the above mentioned aromatic hydrocarbon groups.

In addition to the above-mentioned groups having a substituent, the α-amino acids of α-amino acids having at least one aromatic cyclic group include those protected by a protecting group, and aromatic rings wherein at least one aromatic cyclic group present in the α-amino acid is contained in the substituent or protecting group. Said α-amino acid may be a naturally-occurring α-amino acid (e.g., Gly, Ala, Val, Leu, Ile, Ser, Thr, Glu, Asn, Phe, Trp, Met, His, Cys, Arg, Asn, Gln, Tyr, (I)Tyr, diiodo-Tyr) or a non-naturally-occurring α-amino acid (e.g., Phg, Cha, Nva, Nle, Pya(2), Pya(3), Thi), whether of the L-, D- or DL-configuration. Examples of substituents or protecting groups for the α-amino acid include those present mainly at the 1-carboxyl group thereof, preferably an ester (e.g., benzyl ester, diphenylmethyl ester, trityl ester) or an amide (e.g., phenylamide, benzylamide, diphenylamide, dibenzylamide, 2-phenylethylamide, 2,2-diphenylethylamide, 1,2-diphenylethylamide, indol-3-ylmethylamide, 2-(indol-3-yl)ethylamide) at the carboxyl group. Examples of the amide at the 1-carboxyl group also include amides with an additional α-amino acid. When there is another carboxyl group in addition to the 1-carboxyl group, the substituent or protective group may be an ester (e.g., phenyl ester, benzyl ester, diphenylmethyl ester, trityl ester) or amide (e.g., phenylamide, benzylamide, diphenylmethylamide, diphenylamide, dibenzylamide, 2-phenylethylamide, 2,2-diphenylethylamide, 1,2-diphenylethylamide, indol-3-ylmethylamide, 2-(indol-3-yl)ethylamide) at that carboxyl group. The substituent or protecting group may also be a substituent or protecting group on a functional group other than the carboxyl group (e.g., hydroxyl group, thiol group, amino group) or a substituent on a carbon atom.

Examples of "groups resulting from elimination of one hydrogen atom from the α-amino acid group of α-amino acids having at least one aromatic ring" for X include -Phe-OH, -Tyr-OH, -Trp-OH, -Phg-OH, -(m-F)Tyr-OH, -(p-F)Phe-OH, -(p-Cl)Phe-OH, -(p-Me)Phe-OH, -Trp(Me)-OH, -Trp(CHO)-OH, -Phe-Trp-OH, -Trp-Phe-OH, -Tyr-Trp-OH, -Trp-Phe-OH, -(m-F)Tyr-(p-F)Phe-OH, -Glu(OBzl)-OH, -Glu-OBzl, -Asp(OBzl)-OH, -Asp-Obzl, -Asp-Asp(OBzl)-OH, -Glu(NBzl$_2$)-OH, -Glu(NHBzl)-OH, -Asp(NBzl$_2$)-OH, -Asp(NHBzl)-OH, -Glu-NBzl$_2$, -Glu-NHBzl, -Asp-NBzl$_2$, -Asp-NHBzl, -Glu-NHCHPhCH$_2$Ph, -Asp-NHCHPhCH$_2$Ph, -Glu-NHCH$_2$CHPh$_2$, -Asp-NHCH$_2$CHPh$_2$, -Glu(NHCHPhCH$_2$Ph)-OH, -Asp(NHCHPhCH$_2$Ph)-OH, -Glu(NHCH$_2$CHPh$_2$)-OH, -Asp(NHCH$_2$CHPh$_2$)-OH, -Glu(NHCH$_2$CH$_2$-Ind)-OH, -Asp(NHCH$_2$CH$_2$-Ind)-OH, -Glu-NHCH$_2$CH$_2$-Ind, -Asp-NHCH$_2$CH$_2$-Ind, -Trp-NH-Ind(OH) and -Tyr-Iqu(OH), -(I)Tyr-Phe-OH, -Trp-Trp-OH, -Tyr(Bzl)-Phe-OH, -Tyr(Bzl)-Trp-OH, -(I)Tyr-Trp-OH, -(I)Tyr-Tyr-OH, -Trp-His-OH, -His-Trp-OH, -Tyr-His-OH, %-His-Tyr-OH, -Phe-His-OH, -His-Phe-OH, -Phe-Trp-OH, -Phe-Trp-OH, -Phe-Tyr-OH, -Phe-Phe-OH. The amino acids constituting these groups may be of the L-, D- or DL configuration.

The alkylamino group for the "alkylamino group substituted for by an aromatic cyclic group" for X is specifically a $C_{1-19}$ alkylamino group or a $C_{3-10}$ cycloalkylamino group. The aromatic cyclic group is present as a substituent on carbon or nitrogen of these alkylamino groups (e.g., methylamino, ethylamino, n-propoxylamino, isopropylamino, n-butylamino, isobutylamino, sec-butylamino, tert-butylamino, n-pentylamino, n-hexylamino, n-decylamino, cyclopropylamino, cyclopentylamino, cyclohexylamino, cyclohexylmethylamino, 2-cyclohexylethylamino). Examples of the aromatic cyclic group are the same as specified above. Thus, "the alkylamino group substituted for by an aromatic cyclic group" is execplified by -NBzl$_2$, -NHBzl, -NHCHPhCH$_2$Ph, -NHCH$_2$CHPh$_2$ and -NHCH$_2$CH$_2$-Ind.

With respect to formula [I], $R_6$ represents a hydrogen atom, a lower alkyl group which may be substituted or an aromatic cyclic group which may be substituted. The lower alkyl group is preferably a straight or branched alkyl group having 1 to 6 carbon atoms, including methyl, ethyl, n-propyl, isopropyl, n-butyl, isobutyl, sec-butyl, tert-butyl, n-pentyl, isoamyl, tert-amyl, neopentyl and n-hexyl. These lower alkyl groups may have 1 to 3 substituents. Examples of the substituents include aromatic cyclic groups (e.g., $C_{6-15}$ aromatic hydrocarbon groups and 5- to 6-membered aromatic heterocyclic group which contain 1 to 4 hetero atoms of O, S, N and others and these groups as condensed with another aromatic ring (e.g., benzene ring) such as phenyl, naphthyl, indenyl, furyl, thienyl, pyridyl, quinolyl, pyranyl, imidazolyl, pyrimidyl, purinyl, indolyl), sulfur-containing groups (e.g., thione, mercapto, methylthio, ethylthio, phenylthio), oxygen-containing groups (e.g., ketone, hydroxy, methoxy, ethoxy, phenoxy, benzyloxy) and nitrogen-containing groups (e.g., amino, N-methylamino, methylamino, N-ethylamino, quanidino). The aromatic cyclic group is preferably an aromatic hydrocarbon group or aromatic heterocyclic group which may be substituted. Such an aromatic hydrocarbon group is preferably one having 6 to 12 carbon atoms (e.g., phenyl, 1-naphthyl, 2-naphthyl). The aromatic heterocyclic group is preferably a 5- or 6-membered cyclic group containing 1 to 4 hetero atoms of O, S, N and others and these groups as condensed with the rings such as benzene ring (e.g., furyl, thienyl, pyridyl, thiazolyl, imidazolyl, indolyl). Examples of substituents for these aromatic hydrocarbon groups or aromatic heterocyclic groups include $C_{1-6}$ alkyls (e.g., methyl, ethyl, n-propyl, n-butyl), halogens (e.g., fluorine, chlorine, bromine, iodine), $C_{1-6}$ alkoxys (e.g., methoxy, ethoxy, n-propoxy, isopropoxy, n-butoxy, tert-butoxy), $C_{1-6}$ alkylthios (e.g., methylthio, ethylthio, n-propylthio, isopropylthio, n-butylthio, tert-butylthio), $C_{1-6}$ alkylcarbonyls (e.g., formyl, acetyl), $C_{1-6}$ alkoxycarbonyls (e.g., methoxycarbonyl, ethoxycarbonyl, isopropoxycarbonyl, tert-butoxycarbonyl). The number of the substituents is 1 to 3. R6 is preferably (i) a lower alkyl group (e.g., $C_{1-6}$ alkyl such as methyl, ethyl, n-propyl, isopropyl, n-butyl, isobutyl, sec-butyl, tert-butyl, n-pentyl, isoamyl, tert-amyl, neopentyl or n-hexyl), (ii) 5- to 6-membered aromatic hetero cyclic groups which contain 1 to 4 hetero atoms of O, S, N and others (e.g., furyl, thienyl, pyridyl) or (iii) a lower alkyl group substituted by an aromatic heterocyclic group such as a 5- to 6-membered cyclic group which contain 1 to 4 hetero atoms of O, S, N and others and the group as condensed with another ring (e.g., benzene ring) such as 2-pyridylmethyl, 3-pyridylmethyl, 4-pyridylmethyl, indol-3-ylmethyl, N-methylindol-3-yl-methyl, N-formylindol-3-ylmethyl 2-thienyl-methyl, 3-thienyl-methyl, 2-imidazolyl-methyl. The carbon atom to which R6 is bound is an asymmetric carbon, which may be of the L-, D- or DL configuration, with preference given to the D-configuration. With respect to formula [I], n represents an integer of 0 or more, preferably 0 or 1 to 4, ideally 0. Provided that n is 0, the -N(R$_5$)-CH(R$_6$)-(CH$_2$)n-CO- moiety is represented by -N(R$_5$)-CH(R$_6$)-CO-; therefore, this moiety is an α-amino acid residue (e.g., Ala, Val, Leu, Ile, Trp, Pya(2), Pya(3)), preferably Ala, Trp, Pya(2) or Pya(3). With respect to formula [I], m represents an integer of 2 or more, preferably 2 to 6. -NH-(CH$_2$)m-CO- represents βAla for m=2, GABA for m=3 and εAhx for m=5.

Peptide [I] of the present invention is structurally unique at the -NH-(CH$_2$)m-CO-X moiety. By having at least one aromatic ring at the X moiety, the peptide exhibits marked endothelin receptor-antagonistic action. This contribution of the aromatic ring to endothelin receptor-antagonistic action is evident from comparative data (IC$_{50}$) on peptides having an aromatic ring (compounds of Examples) and those having no aromatic ring (compounds of Reference Examples), as described in Test Example given below. Peptide [I] of the present invention includes salts thereof. Such salts are salts with base when [I] is an acidic compound, and salts with acid when [I] is a basic compound. Example salts of peptide [I] with base include alkali metal salts (e.g., sodium salt, potassium salt), alkaline earth metal salts (e.g., calcium salt, magnesium salt), ammonium salt and organic base salts (e.g., pyridine salt, triethylamine salt). Example salts of peptide [I] with acid include inorganic acid salts (e.g., hydrochloride, sulfate, nitrate) and organic acid salts (e.g., acetate, oxalate, p-toluenesulfonate).

Peptide [I] of the present invention can be produced by a known conventional means of peptide production or a method based thereon, whether it is based on solid-phase synthesis or liquid-phase synthesis, for instance. Accordingly, the desired peptide can be produced by condensing the partial peptide or amino acids capable of constituting the peptide represented by formula [I] and the remaining moiety, and when the product has a protected group, deprotecting the product. Example methods of condensation or deprotection include the following methods ① through ⑤:

① M. Bodanszky and M. A. Ondetti, Peptide Synthesis, Interscience Publishers, New York (1966).

② Schroeder and Luebke, The Peptide, Academic Press, New York (1965).

③ N. Izumiya et al., Peputido Gosei no Kiso to Jukken, Maruzen (1975).

④ H. Yajima and S. Sakakibara, Seikagaku Jikken Koza 1, Tanpakusitsu no Kagaku IV, 205 (1977).

⑤ H. Yajima, Zoku Iyakuhin no Kauhatsu, Vol. 14, Peptide Synthesis, Hirokawa Shoten.

After completion of the reaction, ordinary purifying methods such as solvent extraction, distillation, column chromatography, liquid chromatography and recrystallization can be used in combination to purify and isolate peptide [I].

Effect of the Invention

Peptide [I] of the present invention (including pharmacologically acceptable salts thereof; the same applies below) exhibits endothelin receptor-antagonistic action. The endothelin may, for example, be endothelin-1, -2 or -3 as described in Pharmacia, Vol. 26, pp. 21–24 (1990); the antagonist of the present invention exhibits marked antagonistic action on endothelin-1 and endothelin-2. Peptide [I] is pharmaceutically useful as a prophylactic and therapeutic agent for hypertension, cardiovascular disease and renal disease. For these purposes, peptide [I] may be orally or non-orally administered in the form of a liquid or solid to mammals (e.g., humans, rabbits, dogs, cats, rats, mice). It is a common practice to non-orally administer it in the form of a liquid (e.g., injection). Although the dose volume varies depending on subject, target disease, symptoms, method of administration and other factors, for non-oral use in treating adult hypertension it is advantageous to administer peptide [I] in the form of an injection at about 0.1 to 50 mg, preferably about 0.05 to 20 mg, most preferably 1 to 20 mg, per kg body weight, 1 to 3 times daily by intravenous injection. For oral administration, peptide [I] is administered at about 5 mg to 1 g, preferably about 10 to 100 mg per kg body weight, 1 to 3 times daily. Injections include subcutaneous, intracutaneous, intramuscular and drip infusion injections, as well as intravenous injections. Such injections are prepared by a known method wherein peptide [I] is dissolved, suspended or emulsified in a sterile aqueous or oily solution. Example aqueous solutions for injection include physiological saline and isotonic solutions containing glucose and other auxiliaries, which may be used in combination with appropriate dissolution aids such as alcohols (e.g., ethanol), polyalcohols (e.g., propylene glycol, polyethylene glycol) and nonionic surfactants (e.g., Polysorbate 80, HCO-50). Examples of oily solutions include sesame oil and soybean oil, which may be used in combination with dissolution aids such as benzyl benzoate and benzyl alcohol. The injection thus prepared is usually packaged in an appropriate ampule.

Examples of pharmacologically acceptable salts of peptide [I] which can be used for the endothelin receptor-antagonist of the present invention include alkali metal salts (e.g., sodium salt, potassium salt), alkaline earth metal salts (e.g., calcium salt, magnesium salt), ammonium salts, organic base salts (e.g., pyridine salt, triethylamine salt), inorganic acid salts (e.g., hydrochloride, sulfate, nitrate) and salts of organic acid (e.g., acetate, oxalate, p-toluenesulfonate).

EXAMPLES

The present invention is hereinafter described in more detail by means of the following working examples, reference examples and a test example. In the examples given below, amino acids are of the L-configuration unless otherwise stated.

The conditions of thin-layer chromatography and HPLC used in the examples are as follows:

(1) Thin-layer chromatography (TLC)

Merck Kiesel Gel 60F$_{254}$

Rf1 chloroform-methanol 95:5

Rf2 chloroform-methanol-acetic acid 90:10:5

Rf3 chloroform-methanol-H$_2$O 70:30:5

(2) HPLC

Column: WAKOSIL 5Cl8 (4.6×100 mm)

Eluents: Eluted on a linear density gradient from solution A to solution B (50 minutes)
  Solution A (0.1% aqueous solution of trifluoroacetic acid)
  Solution B (acetonitrile containing 0.1% trifluoroacetic acid)

Flow rate: 1.0 ml/min

Example 1

Production of Boc-Leu-(D)Trp-(D)Ala-βAla-Tyr-(D)Phe-OH

Boc-Tyr-OH (1.41 g) and HONB (1.08 g) were dissolved in acetonitrile (20 ml), and WSCD HCl was added under ice cooling conditions, followed by stirring for about 2 hours. To this solution was added an acetonitrile solution (20 ml) containing H-(D)Phe-OBzl (1.31 g) and triethylamine (0.67 ml), followed by stirring for 4 hours. The solvent was distilled off under reduced pressure, the resulting residue was dissolved in ethyl acetate (80 ml), and N,N-diisopropylethylenediamine (0.2 ml) was added, followed by stirring for 10 minutes. Then the mixture was sequentially washed with a saturated sodium hydrogen carbonate solution, 0.2N hydrochloric acid and pure water and dried over anhydrous sodium sulfate. The solvent was distilled off under reduced pressure to yield a crystal of Boc-Tyr-(D)Phe-Obzl (2.28 g).

TLC:0.52 (Rf1), 0.79 (Rf2)

Boc-Tyr-(D)Phe-Obzl (2.08 g) was dissolved in 4N hydrochloric acid/ethyl acetate (8 ml). After this solution was kept standing at room temperature for 30 minutes, the solvent was distilled off under reduced pressure. The separating crystal was filtered with diethyl ether ad dried, after which it was dissolved in N,N-dimethylformamide (10 ml). To this solution were added an acetonitrile solution (10 ml) of Boc-βAla-ONB which had been synthesized from Boc-βAla-OH (0.84 g), HONB (0.88 g) and WSCD.HCl (0.92 g), and triethylamine (0.60 ml), followed by stirring at room temperature overnight. After the solvent was distilled off under reduced pressure, the residue was dissolved in ethyl acetate (80 ml), and N,N-diisopropylethylenediamine (0.4 ml) was added, followed by stirring for 10 minutes. Then the mixture was sequentially washed with a saturated sodium hydrogen carbonate solution, 0.2N hydrochloric acid and pure water and dried over anhydrous sodium sulfate. The solvent was distilled off under reduced pressure to yield a crystal of Boc-βAla-Tyr-(D)Phe-OBzl (1.48 g).

TLC: 0.38 (Rf1), 0.76 (Rf2)

Boc-βAla-Tyr-(D)Phe-OBzl (1.47 g) was dissolved in 4N hydrochloric acid/ethyl acetate (10 ml). After this solution was kept standing at room temperature for 30 minutes, the solvent was distilled off under reduced pressure. The separating crystal was filtered with diethyl ether and dried, after which it was dissolved in N,N-dimethylformamide (10 ml). To this solution were added an acetonitrile solution (10 ml) of Boc-(D)Ala-ONB which had been synthesized from Boc-(D)Ala-OH (0.52 g), HONB (0.54 g) and WSCD.HCl (0.58 g), and triethylamine (0.37 ml), followed by stirring at room temperature overnight. After the solvent was distilled off under reduced pressure, the residue was dissolved in ethyl acetate (80 ml), and N,N-diisopropylethylenediamine (0.4 ml) was added, followed by stirring for 10 minutes. Then the mixture was sequentially washed with a saturated sodium hydrogen carbonate solution, 0.2N hydrochloric acid and pure water and dried over anhydrous sodium sulfate. The solvent was distilled off under reduced pressure to yield a crystal of Boc-(D)Ala-βAla-Tyr-(D)Phe-Obzl (1.50 g).

TLC: 0.36 (Rf1), 0.76 (Rf2)

Boc-(D)Ala-βAla-Tyr-(D)Phe-OBzl (1.32 g) was dissolved in 4N hydrochloric acid/ethyl acetate (10 ml). After this solution was kept standing at room temperature for 30 minutes, the solvent was distilled off under reduced pressure. The separating crystal was filtered with diethyl ether and dried, after which it was dissolved in N,N-dimethylformamide (10 ml). To this solution were added an acetonitrile solution (10 ml) of Boc-(D)Trp-ONB which had been synthesized from Boc-(D)Trp-OH (0.67 g), HONB (0.43 g) and WSCD.HCl (0.46 g), and triethylamine (0.30 ml), followed by stirring at room temperature overnight. After the solvent was distilled off under reduced pressure, the residue was dissolved in ethyl acetate (80 ml), and N,N-diisopropylethylenediamine (0.4 ml) was added, followed by stirring for 10 minutes. Then the mixture was sequentially washed with a saturated sodium hydrogen carbonate solution, 0.2N hydrochloric acid and pure water and dried over anhydrous sodium sulfate. The solvent was distilled off under reduced pressure to yield a crystal of Boc-(D)Trp-(D)Ala-βAla-Tyr-(D)Phe-OBzl (1.48 g).

TLC: 0.22 (Rf1), 0.75 (Rf2)

Boc-(D)Trp-(D)Ala-βAla-Tyr-(D)Phe-OBzl (1.27 g) was dissolved in 4N hydrochloric acid/ethyl acetate (10 ml). After this solution was kept standing at room temperature for 30 minutes, the solvent was distilled off under reduced pressure. The separating crystal was filtered with diethyl ether and dried, after which it was dissolved in N,N-dimethylformamide (10 ml). To this solution were added an acetonitrile solution (10 ml) of Boc-Leu-ONB which had been synthesized from Boc-Leu-OH.H$_2$O (0.41 g), HONB (0.33 g) and WSCD.HCl (0.35 g), and triethylamine (0.22 ml), followed by stirring at room temperature overnight.

After the solvent was distilled off under reduced pressure, the residue was dissolved in ethyl acetate (80 ml), and N,N-diisopropylethylenediamine (0.4 ml) was added, followed by stirring for 10 minutes. Then the mixture was sequentially washed with a saturated sodium hydrogen carbonate solution, 0.2N hydrochloric acid and pure water and dried over anhydrous sodium sulfate. The solvent was distilled off under reduced pressure to yield a crystal of Boc-Leu-(D)Trp-(D)Ala-βAla-Tyr-(D)Phe-OBzl (1.30 g).

TLC: 0.23 (Rf1), 0.76 (Rf2)

Boc-Leu-(D)Trp-(D)Ala-βAla-Tyr-(D)Phe-OBzl (0.2 g) was dissolved in methanol (50 ml) and then catalytically reduced in a hydrogen stream in the presence of palladium black catalyst. After the catalyst was filtered out and the solvent was distilled off, the residue was dissolved in a 50% aqueous solution of acetic acid (3 ml) and applied to a column (2×95 cm) of Sephadex G-25, packed with 50% aqueous acetic acid, and developed with the same solvent. The major fractions were collected and lyophilized to yield a white powder of Boc-Leu-(D)Trp-(D)Ala-βAla-Tyr-(D)Phe-OH (170 mg).

TLC (Rf2) 0.19, HPCL eluting time 24.6 minutes Mass analysis: $(M+H)^+=870$

Example 2

Production of Boc-Leu-(D)Trp-(D)Ala-βAla-Tyr-Phe-OH

Using H-Phe-OBzl.HCl in place of H-(D)Phe-OBzl.HCl in the production in Example 1, the same procedure as in Example 1 was followed to yield 160 mg of a white powder of Boc-Leu-(D)Trp-(D)Ala-βAla-Tyr-Phe-OH.

TLC (Rf2) 0.19, HPLC eluting time 24.6 minutes Mass analysis: $(M+H)^+=870$

Example 3

Production of Boc-Leu-(D)Trp-(D)Ala-βAla-(D)Try-(D)Phe-OH

Using Boc-(D)Tyr-OH in place of Boc-Tyr-OH in the production in Example 1, the same procedure as in Example 1 was followed to yield 90 mg of a white powder of Boc-Leu-(D)Trp-(D)Ala-βAla-(D)Tyr-(D)Phe-OH.

TLC (Rf2) 0.19, HPLC eluting time 24.4 minutes Mass analysis: $(M+H)^+=870$

Example 4

Production of Boc-Leu-(D)Trp-(D)Ala-βAla-(D)Try-Phe-OH

Using Boc-(D)Tyr-OH in place of Boc-Tyr-OH in the production in Example 2, the same procedure as in Example 1 was followed to yield 87 mg of a white powder of Boc-Leu-(D)Trp-(D)Ala-βAla-(D)Tyr-Phe.

TLC (Rf2) 0.19, HPLC eluting time 24.6 minutes Mass analysis: $(M+H)^+=870$

Example 5

Production of Boc-Leu-(D)Trp-(D)Ala-βAhx-Try-Phe-OH

Using Boc-εAhx-OH in place of Boc-βAla-OH in the production in Example 2, the same procedure as in Example 1 was followed to yield 116 mg of a white powder of Boc-Leu-(D)Trp-(D)Ala-εAhx-Tyr-Phe-OH.

TLC (Rf2) 0.20, HPLC eluting time 24.9 minutes Mass analysis: $(M+H)^+=912.1$

Example 6

Production of Boc-Leu-(D)Trp-(D)Trp-βAla-Try-Phe-OH

Using Boc-(D)Tyr-OH in place of Boc-(D)Ala-OH in the production in Example 2, the same procedure as in Example 1 was followed to yield 106 mg of a white powder of Boc-Leu-(D)Trp-(D)Trp-βAla-Tyr-Phe-OH.

TLC (Rf2) 0.26, HPLC eluting time 26.8 minutes Mass analysis: $(M+H)^+=986.1$

Example 7

Production of Boc-Leu-(D)Trp-(D)Ala-βAla-(D)Try-OH

Using Boc-(D)Tyr-OBzl in place of Boc-Tyr-(D)Phe-OBzl in the production in Example 2, the same procedure as in Example 1 was followed to yield 126 mg of a white powder of Boc-Leu-(D)Trp-(D)Ala-βAla-(D)Tyr-OH.

TLC (Rf2) 0.23, HPLC eluting time 22.2 minutes Mass analysis: $(M+H)^+=723.8$

Example 8

Production of Boc-Leu-(D)Trp-(D)Ala-βAla-Tyr-OH

Using Boc-Tyr-OBzl in place of Boc-Tyr-(D)Phe-OBzl in the production in Example 1, the same procedure as in Example 1 was followed to yield 60 mg of a white powder of Boc-Leu-(D)Trp-(D)Ala-βAla-Tyr-OH.

TLC (Rf2) 0.23, HPLC eluting time 22.4 minutes Mass analysis: $(M+H)^+=723.7$

Example 9

Production of Boc-Leu-(D)Trp-(D)Ala-βAla-(D)Phe-OH

Using Boc-(D)Phe-OBzl in place of Boc-Tyr-(D)Phe-Obzl in the production in Example 2, the same procedure as in Example 1 was followed to yield 96 mg of a white powder of Boc-Leu-(D)Trp-(D)Ala-βAla-(D)Phe-OH.

TLC (Rf2) 0.24, HPLC eluting time 24.5 minutes Mass analysis: $(M+H)^+=707.8$

Example 10

Production of Boc-Leu-(D)Trp-(D)Ala-αAla-Phe-OH

Using Boc-Phe-OBzl in place of Boc-Tyr-(D)-Phe-OBzl in the production in Example 1, the same procedure as in Example 1 was followed to yield 113 mg of a white powder of Boc-Leu-(D)Trp-(D)Ala-βAla-Phe.

TLC (Rf2) 0.24, HPLC eluting time 24.5 minutes Mass analysis: $(M+H)^+=707.8$

Example 11

Production of Boc-Leu-(D)Trp-(D)Ala-βAla-(D)(m-F)Tyr-OH

Using Boc-(D)(m-F)Tyr-OBzl in place of Boc-Tyr-(D)Phe-Obzl in the production in Example 1, the same procedure as in Example 1 was followed to yield 97 mg of a white powder of Boc-Leu-(D)Trp-(D)Ala-βAla-(D)(m-F)Tyr-OH.

TLC (Rf2) 0.26, HPLC eluting time 22.5 minutes Mass analysis: $(M+H)^+=741.3$

Example 12

Production of Boc-Leu-(D)Trp-(D)Ala-βAla-(m-F)Tyr-OH

Using Boc-(m-F)Tyr-OBzl in place of Boc-Tyr-(D)Phe-OBzl in the production in Example 1, the same procedure as in Example 1 was followed to yield 108 mg of a white powder of Boc-Leu-(D)Trp-(D)Ala-βAla-(m-F)Tyr-OH.

TLC (Rf2) 0.26, HPLC eluting time 22.5 minutes Mass analysis: $(M+H)^+=741.3$

Example 13

Production of Boc-Leu-(D)Trp-(D)Ala-βAla-(D)(p-F)Phe-OH

Using Boc-(D)(p-F)Phe-OBzl in place of Boc-Tyr-(D)Phe-OBzl in the production in Example 1, the same procedure as in Example 1 was followed to yield 145 mg of a white powder of Boc-Leu-(D)Trp-(D)Ala-βAla-(D)(p-F)Phe-OH.

TLC (Rf2) 0.41, HPLC eluting time 24.9 minutes Mass analysis: (M+H)⁺=725.8

Example 14

Production of Boc-Leu-(D)Trp-(D)Ala-βAla-(p-F)Phe-OH

Using Boc-(p-F)Phe-OBzl in place of Boc-Tyr-(D)Phe-Obzl in the production in Example 1, the same procedure as in Example 1 was followed to yield 89 mg of a white powder of Boc-Leu-(D)Trp-(D)Ala-βAla-(D)(p-F)Phe-OH.

TLC (Rf2) 0.41, HPLC eluting time 24.9 minutes Mass analysis: (M+H)⁺=725.8

Example 15

Production of Boc-Leu-(D)Trp-(D)Ala-βAla-(D)Phg-OH

Using Boc-(D)Phg-OBzl in place of Boc-Tyr-(D)Phe-Obzl in the production in Example 1, the same procedure as in Example 1 was followed to yield 49 mg of a white powder of Boc-Leu-(D)Trp-(D)Ala-βAla-(D)Phg-OH.

TLC (Rf2) 0.24, HPLC eluting time 24.1 minutes Mass analysis: (M+H)⁺=693.3

Example 16

Production of Boc-Leu-(D)Trp-(D)Ala-βAla-Trp-OH

Using Boc-Trp-OBzl in place of Boc-Tyr-(D)Phe-OBzl in the production in Example 1, the same procedure as in Example 1 was followed to yield 198 mg of a white powder of Boc-Leu-(D)Trp-(D)Ala-βAla-Trp-OH.

TLC (Rf2) 0.27, HPLC eluting time 24.3 minutes Mass analysis: (M+H)⁺=746.3

Example 17

Production of Boc-Leu-(D)Trp-(D)Ala-βAla-Tyr-(D)Trp-OH

Using Boc-(D)Trp-OBzl.HCl in place of H-(D)Phe-OBzl.HCl in the production in Example 1, the same procedure as in Example 1 was followed to yield 160 mg of a white powder of Boc-Leu-(D)Trp-(D)Ala-βAla-Tyr-(D)Trp-OH.

TLC (Rf2) 0.19, HPLC eluting time 27.0 minutes Mass analysis: (M+H)⁺=909.5

Example 18

Production of Boc-Leu-(D)Trp-(D)Ala-βAla-Trp-(D)Phe-OH

Using Boc-Trp-OH in place of Boc-Tyr-OH in the production in Example 1, the same procedure as in Example 1 was followed to yield 203 mg of a white powder of Boc-Leu-(D)Trp-(D)Ala-βAla-Trp-(D)Phe-OH.

TLC (Rf2) 0.26, HPLC eluting time 26.4 minutes Mass analysis: (M+H)⁺=893.5

Example 19

Production of Adamantan-1-ylcarbonyl-Leu-(D)Trp-(D)Ala-βAla-Tyr-(D)Phe-OH

Boc-Leu-(D)Trp-(D)Ala-βAla-Tyr-(D)Phe-OBzl (0.1 g) was dissolved in 4N hydrochloric acid/ethyl acetate (1 ml). After this solution was kept standing at room temperature for 30 minutes, the solvent was distilled off under reduced pressure. The residue was filtered with diethyl ether and dried, after which it was dissolved in N,N-dimethylformamide (1 ml). After neutralization of this solution by the addition of triethylamine (15µ), adamantan-1-ylcarbonyl chloride (25 mg) was added, followed by stirring for 3 hours. After the solvent was distilled off under reduced pressure, the residue was dissolved in ethyl acetate (20 ml) and sequentially washed with a saturated sodium hydrogen carbonate solution, 0.2N hydrochloric acid and pure water, and dried over anhydrous sodium sulfate. The solvent was distilled off under reduced pressure to yield a powder of adamantan-1-ylcarbonyl-Leu-(D)Trp-(D)Ala-βAla-Tyr-(D)Phe-OBzl (0.1 g). This powder was dissolved in methanol (50 ml) and then catalytically reduced in a hydrogen stream in the presence of palladium black catalyst. After the catalyst was filtered out and the solvent was distilled off, the residue was dissolved in a 50% aqueous solution of acetic acid (3 ml) and applied to a column (2×95 cm) of 50% Sephadex G-25, packed with 50% aqueous acetic acid, and developed with the same solvent. The major fractions were collected and lyophilized to yield a white powder of adamantan-1-ylcarbonyl-Leu-(D)Trp-(D)Ala-βAla-Tyr-(D)-Phe-OH (70 mg).

TLC (Rf2) 0.22, HPLC eluting time 26.7 minutes Mass analysis: (M+H)⁺=932.5

Example 20

Production of Adamantan-1-ylcarbonyl-Leu-(D)Trp-(D)Ala-βAla-Tyr-Phe-OH

Boc-Leu-(D)Trp-(D)Ala-βAla-Tyr-Phe-OBzl was reacted in the same manner as in Example 19 to yield 50 mg of a white powder of adamantan-1-ylcarbonyl-Leu-(D)Trp-(D)Ala-βAla-Tyr-Phe.

TLC (Rf2) 0.22, HPLC eluting time 26.7 minutes Mass analysis: (M+H)⁺=932.4

Example 21

Production of (1S)-(–)-Camphanyl-Leu-(D)Trp-(D)Ala-βAla-Tyr-(D)Phe-OH

Boc-Leu-(D)Trp-(D)Ala-βAla-Tyr-(D)Phe-OBzl was reacted with (1S)-(–)-Camphanyl chloride in the same manner as in Example 19 to yield 50 mg of a white powder of (1S)-(–)-Camphanyl-Leu-(D)Trp-(D)Ala-βAla-Tyr-(D)Phe-OH.

TLC (Rf2) 0.23, HPLC eluting time 26.5 minutes Mass analysis: (M+H)⁺=951.1

Example 22

Production of Boc-Leu-(D)Trp-(D)Ala-βAla-Glu(OBzl)-OH

Using Boc-Glu(OBzl)-OPac in place of Boc-Tyr-(D)Phe-OBzl in the production in Example 1, the same procedure as in Example 1 was followed to yield Boc-Leu-(D)Trp-(D)Ala-βAla-Glu(OBzl)-OPac, which was dissolved in 90% acetic acid and treated with zinc powder at room temperature for 1 hour, after which it was applied to a column (2×95 cm) of Sephadex G-25, packed with 50% aqueous acetic acid, and developed with the same solvent. The major fractions were collected and lyophilized to yield a white powder of Boc-Leu-(D)Trp-(D)Ala-βAla-Glu(OBzl)-OH (30 mg).

TLC (Rf2) 0.20, HPLC eluting time 25.3 minutes Mass analysis: (M+H)⁺=779.2

Example 23

Production of Boc-Leu-(D)Trp-(D)Ala-βAla-Glu-OBzl

Using Boc-Glu(OPac)-Obzl in place of Boc-Glu(OBzl)-OPac in the production in Example 22, the same procedure as in Example 22 was followed to yield 53 mg of a white powder of Boc-Leu-(D)Trp-(D)Ala-βAla-Glu-OBzl.

TLC (Rf2) 0.19, HPLC eluting time 25.1 minutes Mass analysis: (M+H)⁺=779.2

Example 24

Production of Boc-Leu-(D)Trp-(D)Ala-βAla-(D)Asp(OBzl)-OH

Using Boc-(D)Asp(OBzl)-OPac in place of Boc-Glu-(OBzl)-OPac in the production in Example 22, the same procedure as in Example 22 was followed to yield 59 mg of a white powder of Boc-Leu-(D)Trp-(D)Ala-βAla-(D)Asp(OBzl)-OH.

TLC (Rf2) 0.19, HPLC eluting time 25.7 minutes Mass analysis: $(M+H)^+=765.1$

Example 25

Production of Boc-Leu-(D)Trp-(D)Ala-βAla-(D)Asp-OBzl

Using Boc-(D)Asp(OPac)-OBzl in place of Boc-Glu-(OBzl)-OPac in the production in Example 22, the same procedure as in Example 22 was followed to yield 65 mg of a white powder of Boc-Leu-(D)Trp-(D)Ala-βAla-(D)Asp-OBzl.

TLC (Rf2) 0.19, HPLC eluting time 25.7 minutes Mass analysis: $(M+H)^+=765.1$

Example 26

Production of Boc-Leu-(D)Trp-(D)Ala-βAla-Glu-NHCHPhCH$_2$Ph

Using Boc-Glu(OBzl)-NHCHPhCH$_2$Ph which had been synthesized from Boc-Glu(OBzl)-OH and 1,2-diphenylethylamine in place of Boc-Tyr-(D)Phe-OBzl in the production in Example 1, the same procedure as in Example 1 was followed to yield 45 mg of a white powder of Boc-Leu-(D)Trp-(D)Ala-βAla-Glu-NHCHPhCH$_2$Ph.

TLC (Rf2) 0.25, HPLC eluting time 26.9 minutes Mass analysis: $(M+H)^+=868.6$

Example 27

Production of Boc-Leu-(D)Trp-(D)Ala-εAhx-Glu-NHCH$_2$CHPh$_2$

Using Boc-Glu(OBzl)-NHCH$_2$CHPh$_2$ which had been synthesized from Boc-Glu(OBzl)-OH and 2,2-diphenylethylamine in place of Boc-Tyr-Phe-OBzl in the production in Example 5, the same procedure as in Example 1 was followed to yield 65 mg of white powder of Boc-Leu-(D)Trp-(D)Ala-εAhx-Glu-NHCH$_2$CHPh$_2$.

TLC (Rf2) 0.27, HPLC eluting time 26.9 minutes Mass analysis: $(M+H)^+=910.6$

Example 28

Production of Boc-Leu-(D)Trp-(D)Ala-εAhx-Asp-NHCHPhCH$_2$Ph

Using Boc-Asp(OBzl)-NHCHPhCH$_2$Ph which has been synthesized from Boc-Asp(OBzl)-OH and 1,2-diphenylethylamine in place of Boc-Glu(OBzl)-NHCH$_2$CHPh$_2$ in the production in Example 27, the same procedure as in Example 1 was followed to yield 66 mg of a white powder of Boc-Leu-(D)Trp-(D)-Ala-εAhx-Asp-NHCHPhCH$_2$Ph.

TLC (Rf2) 0.27, HPLC eluting time 26.7 minutes Mass analysis: $(M+H)^+=896.9$

Example 29

Production of Boc-Leu-(D)Trp-(D)Ala-βAla-Asp-NHCH$_2$CHPh$_2$

Using Boc-Asp(OBzl)-NHCH$_2$CHPh$_2$ which had been synthesized from Boc-Asp(OBzl)-OH and 2,2-diphenylethylamine in place of Boc-Glu(OBzl)-NHCHPhCH$_2$Ph in the production in Example 26, the same procedure as in Example 1 was followed to yield 78 mg of a white powder of Boc-Leu-(D)Trp-(D)Ala-βAla-Asp-NHCH$_2$CHPh$_2$.

TLC (Rf2) 0.28, HPLC eluting time 26.6 minutes Mass analysis: $(M+H)^+=854.9$

Example 30

Production of Boc-Leu-(D)Trp-(D)Ala-βAla-Asp-NHCH$_2$CH$_2$-Ind

Using Boc-Asp(OBzl)-NHCH$_2$CH$_2$-Ind which had been synthesized from Boc-Asp(OBzl)-OH and 2-(indol-3-yl)ethylamine in place of Boc-Glu(OBzl)-NHCHPhCH$_2$Ph in the production in Example 26, the same procedure as in Example 1 was followed to yield 115 mg of a white powder of Boc-Leu-(D)Trp-(D)Ala-βAla-Asp-NHCH$_2$CH$_2$-Ind.

TLC (Rf2) 0.17, HPLC eluting time 24.5 minutes Mass analysis: $(M+H)^+=817.9$

Example 31

Production of Boc-Leu-(D)Trp-(D(Ala-βAla-Asp(NHCH$_2$CH$_2$-Ind)

Using Boc-Asp(NHCH$_2$CH$_2$-Ind)-OBzl in place of Boc-Asp(OBzl)-NHCH$_2$CH$_2$-Ind in the production in Example 30, the same procedure as in Example 1 was followed to yield 86 mg of a white powder of Boc-Leu-(D)Trp-(D)Ala-βAla-Asp(NHCH$_2$CH$_2$-Ind).

TLC (Rf2) 0.18, HPLC eluting time 24.5 minutes Mass analysis: $(M+H)^+=817.8$

Example 32

Production of Boc-Leu-(D)Trp-(D)Ala-βAla-Glu-Asp(N-Bzl$_2$)-NHCH$_2$CH$_2$-Ind

Using Boc-Glu(OBzl)-Asp(NBzl$_2$)-NHCH$_2$CH$_2$-Ind in place of Boc-Asp(OBzl)-NHCH$_2$CH$_2$-Ind in the production in Example 30, the same procedure as in Example 1 was followed to yield 100 mg of a white powder of Boc-Leu-(D)Trp-(D)Ala-βAla-Glu-Asp(NBzl$_2$)-NHCH$_2$CH$_2$-Ind.

TLC (Rf2) 0.25, HPLC eluting time 28.8 minutes Mass analysis: $(M=H)^+=1125.9$

Example 33

Production of Boc-Leu-(D)Trp-(D)Ala-βAla-Glu-Asp(NHCH$_2$CH$_2$-Ind)-NBzl$_2$

Using Boc-Leu-(D)Trp-(D)Ala-βAla-Glu-Asp(NHCH$_2$CH$_2$-Ind)-NBzl$_2$ in place of Boc-Asp(NHCH$_2$CH$_2$-Ind)-OBzl in the production in Example 31, the same procedure as in Example 1 was followed to yield 92 mg of a white powder of Boc-Leu-(D)Trp-(D)Ala-βAla-Glu-Asp(NHCH$_2$CH$_2$-Ind)-NBzl$_2$.

TLC (Rf2) 0.26, HPLC eluting time 28.8 minutes analysis: $(M+H)^+=1126.0$

Example 34

Production of Boc-Leu-(D)Trp-(D)Ala-βAla-Glu-Asp-NBzl$_2$

Using Boc-Asp(OBzl)-NBzl$_2$ in place of Boc-Asp(OBzl)-NHCH$_2$CH$_2$-Ind in the production in Example 30, the same procedure as in Example 1 was followed to yield 68 mg of a white powder of Boc-Leu-(D)Trp-(D)Ala-βAla-Asp-NBzl$_2$.

TLC (Rf2) 0.21, HPLC eluting time 26.9 minutes Mass analysis: $(M+H)^+=854.4$

Example 35

Production of Boc-Leu-(D)Trp-(D)Ala-GABA-Tyr-Phe-OH

Using Boc-GABA-OH in place of Boc-βAla-OH in the production in Example 2, the same procedure as in Example 1 was followed to yield 160 mg of a white powder of Boc-Leu-(D)Trp-(D)Ala-GABA-Tyr-Phe-OH.

TLC (Rf2) 0.20, HPLC eluting time 24.8 minutes Mass analysis: (M+H)$^+$=884.9

Example 36

Production of Boc-Leu-(D)Trp-(D)Ala-εAhx-NHCHPhCH$_2$Ph

Using 1,2-diphenylethylamine in place of H-Tyr-Phe-OBzl in the production in Example 5, the same procedure as in Example 1 was followed to yield 89 mg of a white powder of Boc-Leu-(D)Trp-(D)Ala-εAhx-NHCHPhCH$_2$Ph without catalytic reduction.

TLC (Rf2) 0.32, HPLC eluting time 28.5 minutes Mass analysis: (M+H)$^+$=781.4

Example 37

Production of Boc-Leu-(D)Trp-(D)Ala-εAhx-NHCH$_2$CHPh$_2$

Using 2,2-diphenylethylamine in place of 1,2-diphenylethylamine in the production in Example 36, the same procedure as in Example 36 was followed to yield 91 mg of a white powder of Boc-Leu-(D)Trp-(D)Ala-εAhx-NHCH$_2$CHPh$_2$.

TLC (Rf2) 0.32, HPLC eluting time 28.4 minutes Mass analysis: (M+H)$^+$=781.4

Example 38

Production of Boc-Leu-(D)Trp-(D)Ala-βAla-(m-F)Tyr-(p-F)Phe-OH

Using Boc-(m-F)Tyr-OH and H-(p-F)Phe-OBzl.HCl in place of Boc-Tyr-OH and H-(D)Phe-OBzl.HCl, respectively, in the production in Example 1, the same procedure as in Example 1 was followed to yield 106 mg of a white powder of Boc-Leu-(D)Trp-(D)Ala-βAla-(m-F)Tyr-(p-F)Phe-OH.

TLC (Rf2) 0.22, HPLC eluting time 25.1 minutes Mass analysis: (M+H)$^+$=906.5

Example 39

Production of Hexamethyleneimino-OC-Leu-(D)Trp-(D)Ala-βAla-Tyr-(D)Phe-OH

Using hexamethyleneimino-CO-Leu-OH produced from hexamethyleneimino-CO-Leu-OBzl, which can be produced from hexamethyleneimine and N-carbonyl-Leu-OBzl or from hexamethyleneimine, Leu-OBzl and carbonyldiimidazole, in place of Boc-Leu-OH.H$_2$O in the production in Example 1, the corresponding amine component (H-(D)Trp-(D)Ala-βAla-Tyr-(D)Phe-OBzl) of Example 1 and triethylamine were dissolved in N,N-dimethylformamide, and this solution was condensed with HONB and WSCD.HCl to yield hexamethyleneimino-CO-Leu-(D)Trp-(D)Ala-βAla-Tyr-(D)Phe-OBzl, which was treated in the same manner as with Boc-Leu-(D)Trp-(D)Ala-βAla-Tyr-(D)Phe-OBzl in Example 1 to yield 62 mg of a white powder of hexamethyleneimino-CO-Leu-(D)Trp-(D)Ala-βAla-Tyr-(D)Phe-OH.

TLC: 0.18 (Rf2), 0.44 (Rf3) HPLC eluting time: 24.2 minutes Mass analysis: (M+H)$^+$=895.4

Example 40

Production of Hexamethyleneimino-CO-Leu-(D)Trp-(D)Ala-βAla-Tyr-(D)Phe-ONa

Hexamethyleneimino-CO-Leu-(D)Trp-(D)Ala-βAla-Tyr-(D)Phe-OBzl as described in Example 39 was dissolved in methanol (1 mmol/45 ml), and the ester was hydrolyzed with a 5-fold amount of 1N-NaOH. After neutralizing the excess alkali with a 4-fold amount of 1N-HCl, the solvent was distilled off under reduced pressure. The residue was diluted to about 10$^{-2}$M with distilled water and then applied to a column of Diaion HP-20. After the column was thoroughly washed with distilled water, elution was conducted with 80% aqueous methanol. The desired fraction was collected and concentrated and then subjected to column chromatography using a column of Sephadex LH-20, packed using 50% methanol; the major fraction was collected and lyophilized to yield 50 mg of a white powder.

Na content determined by atomic absorption spectrometry: 2.5%

Example 41

Production of Hexamethyleneimino-CO-Leu-(D)Trp-(D)Ala-βAla-Tyr-Phe-OH

Using H-(D)Trp-(D)Ala-βAla-Tyr-Phe-OBzl, the intermediate used in the production in Example 2, in place of the mine component H-(D)Trp-(D)Ala-βlAla-Tyr-(D)Phe-OBzl in the production of Example 39, the same procedure as in Example 39 was followed to yield 120 mg of a white powder of hexamethyleneimino-CO-Leu-(D)Trp-(D)Ala-βAla-Tyr-Phe-OH.

TLC: 0.24 (Rf2), 0.44 (Rf3) HPLC eluting time: 24.2 minutes Mass analysis: (M+H)$^+$=895.4

Example 42

Production of Hexamethyleneimino-CO-Leu-(D)Trp-Ala-βAla-Tyr-(D)Phe-OH

Using H-(D)Trp-Ala-βlAla-Tyr-(D)Phe-OBzl, the intermediate prepared using Boc-Ala-OH in place of Boc-(D)Ala-OH in the production in Example 1, in place of the amine component H-(D)Trp-(D)Ala-βlAla-Tyr-(D)Phe-OBzl in the production in Example 39, the same procedure as in Example 39 was followed to yield 35 mg of white powder of hexamethyleneimino-CO-Leu-(D)Trp-Ala-βAla-Tyr-(D)Phe-OH.

TLC: 0.22 (Rf2), 0.45 (Rf3) HPLC eluting time: 24.3 minutes Mass analysis: (M+H)$^+$=895.4

Example 43

Production of Hexamethyleneimino-CO-Leu-(D)Trp-(D)Ala-βAla-Tyr(I)-(D)Phe-OH

Using H-(D)Trp-(D)Ala-βAla-Tyr(I)-(D)Phe-OBzl, the intermediate prepared using Boc-Tyr-(I)-OH in place of Boc-Tyr-OH in the production in Example 1, in place of the amine component H-(D)Trp-(D)Ala-βlAla-Tyr-(D)Phe-OBzl in the production in Example 39, the same procedure as in Example 39 was followed to yield hexamethyleneimino-CO-Leu-(D)Trp-Ala-βAla-Tyr-(D)Phe-OBzl, which was dissolved in methanol, and the ester was hydrolyzed with a 5-fold amount of 1N-NaOH. After neutralization with a 5-fold amount of 1N-HCl, the solvent was distilled off under reduced pressure. The residue was applied to a column (2×95 cm) of Sephadex G-25, packed using 50% aqueous acetic acid, and developed with the same solvent. The major fraction was collected and lyophilized to yield 72 mg of a white powder of hexamethyleneimino-CO-Leu-(D)Trp-(D)Ala-βAla-Tyr(I)-(D)Phe-OH.

TLC: 0.21 (Rf2) HPLC eluting time: 25.7 minutes Mass analysis: (M+H)$^+$=1021.4

Example 44

Production of Hexamethyleneimino-CO-Leu-(D)Trp-(D)Thg(2)-βAla-Tyr-(D)Phe-OH

Using H-(D)Trp-(D)Thg(2)-βAla-Tyr-(D)Phe-OBzl, the intermediate prepared using Boc-(D)Thg(2)-OH in place of Boc-(D)Ala-OH in the production in Example 1, in place of the amine component H-(D)Trp-(D)Ala-βlAla-Tyr-(D)Phe-OBzl in the production in Example 39, the same procedure as in Example 39 was followed to yield hexamethyleneimino-CO-Leu-(D)Trp-(D)Thg(2)-βAla-Tyr-(D)Phe-OBzl, which was subjected to the same ester hydrolysis and purification procedures as in Example 43 to yield 80 mg of a white powder of hexamethyleneimino-CO-Leu-(D)-Trp-(D)Thg(2)-βAla-Tyr-(D)Phe-OH.

TLC: 0.20 (Rf2) HPLC eluting time: 25.5 minutes Mass analysis: $(M+H)^+=963.5$

Example 45

Production of Hexamethyleneimino-CO-Leu-(D)Trp-(D)Thg(3)-βAla-Tyr-(D)Phe-OH

Using Boc-(D)Thg(3) in place of Boc-(D)Thg(2)-OH in the production in Example 44, the same procedure as in Example 44 was followed to yield 45 mg of a white powder in hexamethyleneimino-CO-Leu-(D)Trp-(D)Thg(3)-βAla-Tyr-(D)Phe-OH.

TLC: 0.20 (Rf2) HPLC eluting time: 25.6 minutes Mass analysis: $(M+H)^+=963.5$

Example 46

Production of Hexamethyleneimino-CO-Leu-(D)Trp-(D)Thi-βAla-Tyr-(D)Phe-OH

Using Boc-(D)Thi-OH in place of Boc-(D)Thg(2)-OH in the production in Example 44, the same procedure as in Example 44 was followed to yield 45 mg of a white powder of hexamethyleneimino-CO-Leu-(D)Trp-(D)Thi-βAla-Tyr-(D)Phe-OH.

TLC: 0.23 (Rf2), 0.52 (Rf3) HPLC eluting time: 26.1 minutes Mass analysis: $(M+H)^+=977.4$

Example 47

Production of Hexamethyleneimino-CO-Leu-(D)Trp-(D)Ala-βAla-Tyr-(D)Phe-εAhx-OH

Using the amine component obtained using H-(D)Phe-εAhx-OBzl.HCl produced from Boc-(D)Phe-OH and H-εAhx-OBzl.HCl in place of H-(D)Phe-OBzl.HCl in the production in Example 1, the same procedure as in Example 39 was followed to yield 72 mg of a white powder of hexamethyleneimino-CO-Leu-(D)Trp-(D)Ala-βAla-Tyr-(D)Phe-εAhx-OH.

TLC: 0.33 (Rf2) HPLC eluting time: 24.1 minutes Mass analysis: $(M+H)^+=1008.4$

Example 48

Production of Hexamethyleneimino-CO-Leu-(D)Trp-(D)Ala-βAla-Tyr-(D)Phe-βAla-OH

Using the amine component obtained using H-(D)Phe-βAla-OBzl.HCl produced from Boc-(D)Phe-OH and H-βAla-OBzl.HCl in place of H-(D)Phe-OBzl.HCl in the production in Example 1, the same procedure as in Example 39 was followed to yield 68 mg of a white powder of hexamethyleneimino-CO-Leu-(D)Trp-(D)Ala-βAla-Tyr-(D)Phe-βAla-OH.

TLC: 0.22 (Rf2)

HPLC eluting time: 23.4 minutes Mass analysis: $(M+H)^+=966.5$

Example 49

Production of Hexamethyleneimino-CO-Leu-(D)Trp-(D)Ala-βAla-Trp-NH-Ind-OH

Using H-(D)Trp-(D)Ala-βlAla-Trp-NH-Ind-OCH₃, the intermediate prepared using Boc-Trp-OH and NH₂-Ind-OCH₃ in place of Boc-Tyr-OH and H-(D)Phe-OBzl.HCl, respectively, in the production in Example 1, in place of the amine component H-(D)Trp-(D)Ala-βlAla-Tyr-(D)Phe-OBzl in the production in Example 39, the same procedure as in Example 39 was followed to yield hexamethyleneimino-CO-Leu-(D)Trp-(D)Ala-βAla-Trp-NH-Ind-OCH₃, which was subjected to the same ester hydrolysis and purification procedures as in Example 43 to yield 30 mg of a white powder of hexamethyleneimino-CO-Leu-(D)Trp-(D)Ala-βAla-Trp-NH-Ind-OH.

TLC: 0.30 (Rf2) HPLC eluting time: 26.2 minutes Mass analysis: $(M+H)^+=930.4$

Example 50

Production of hexamethyleneimino-CO-LEU-(D)Trp-(D)Ala-βAla-Iqu-(D)Trp-OH

Using H-(D)Trp-(D)Ala-βlAla-Iqu-(D)Trp-OCCH₃, the intermediate prepared using Boc-Iqu-OH and H-(D)Trp-OCH₃.HCl in place of Boc-Tyr-OH and H-(D)Phe-OBzl.HCl, respectively, in the production in Example 1, in place of the amine component H-(D)Trp-(D)Ala-βlAla-Tyr-(D)Phe-OBzl in the production in Example 39, the same procedure as in Example 39 was followed to yield hexamethyleneimino-CO-Leu-(D)Trp-(D)Ala-βAla-Iqu-(D)Trp-OCH₃, which was subjected to the same ester hydrolysis and purification procedures as in Example 43 to yield 43 mg of a white powder of hexamethyleneimino-CO-Leu-(D)Trp-(D)Ala-βAla-Iqu-(D)Trp-OH.

TLC: 0.25 (Rf2), 0.55 (Rf3) HPLC eluting time: 26.3 minutes Mass analysis: $(M+H)^+=930.4$

Example 51

Production of Hexamethyleneimino-CO-Leu-(D)Trp-(D)His-βAla-Tyr-(D)Phe-OH

Using H-(D)Trp-(D)His-βlAla-Tyr-(D)Phe-OBzl, the intermediate prepared using Boc-(D)His(Boc)-OH in place of Boc-(D)Ala-OH in the production in Example 1, in place of the amine component H-(D)Trp-(D)Ala-βlAla-Tyr-(D)Phe-OBzl in the production in Example 39, the same procedure as in Example 39 was followed to yield 30 mg of a white powder of hexamethyleneimino-CO-Leu-(D)His-βAla-Tyr-(D)Phe-OH.

TLC: 0.49 (Rf3) HPLC eluting time: 22.8 minutes Mass analysis: $(M+H)^+=961.6$

Example 52

Production of Cyclohexyl-NH-CO-Leu-(D)Trp-(D)Ala-βAla-Tyr-(D)Phe-OH

Using cyclohexyl isocyanate in place of adamantan-1-ylcarbonyl chloride in the production in Example 19, the same procedure as in Example 19 was followed to yield 54 mg of a white powder of cyclohexyl-NH-CO-Leu-(D)Trp-(D)Ala-βAla-Tyr-(D)Phe-OH.

TLC: 0.17 (Rf2) HPLC eluting time: 24.3 minutes Mass analysis: $(M+H)^+=895.4$

Example 53

Production of Dicyclohexyl-NH-CO-Leu-(D)Trp-(D)Ala-βAla-Tyr-(D)Phe-OH

Using dicyclohexylamine in place of hexamethyleneimine in the production in Example 39, the same procedure as in Example 39 was followed to yield 73 mg of a white powder of dicyclohexyl-NH-CO-Leu-(D)Trp-(D)Ala-βAla-Tyr-(D)Phe-OH.

TLC: 0.20 (Rf2) HPLC eluting time: 24.8 minutes Mass analysis: $(M+H)^+=977.6$

Example 54

Production of Me-Pip-CO-Leu-(D)Trp-(D)Ala-βAla-Tyr-(D)Phe-OH

Using 1-methylpiperazine in place of hexamethyleneimine in the production in Example 39, the same procedure as in Example 39 was followed to yield 84 mg of a white powder of Me-Pip-CO-Leu-(D)Trp-(D)Ala-βAla-Tyr-(D)Phe-OH.

TLC: 0.28 (Rf3) HPLC eluting time: 20.8 minutes Mass analysis: $(M+H)^+=896.2$

Example 55

Production of Pym-Pip-CO-Leu-(D)Trp-(D)Ala-βAla-Tyr-(D)Phe-OH

Using 1-(2-pyrimidyl)piperazine in place of hexamethyleneimine in the production in Example 39, the same procedure as in Example 39 was followed to yield 55 mg of a white powder of Pym-Pip-CO-Leu-(D)Trp-(D)Ala-βAla-Tyr-(D)Phe-OH.

TLC: 0.14 (Rf2), 0.49 (Rf3) HPLC eluting time: 22.0 minutes Mass analysis: $(M+H)^+=960.5$

Example 56

Production of PhCH$_2$NH-CO-Leu-(D)Trp-(D)Ala-βAla-Tyr-(D)Phe-OH

Using benzylamine in place of hexamethyleneimine in the production in Example 39, the same procedure as in Example 39 was followed to yield 91 mg of a white powder of PhCH$_2$NH-CO-Leu-(D)Trp-(D)Ala-βAla-Tyr-(D)Phe-OH.

Mass analysis: $(M+H)^+=903.5$

Example 57

Production of 2-Furyl-CO-Leu-(D)Trp-(D)Ala-βAla-Tyr-(D)Phe-OH

Using 2-furoyl chloride in place of adamantan-1-ylcarbonyl chloride in the production in Example 19, the same procedure as in Example 19 was followed to yield 70 mg of a white powder of 2-furyl-CO-Leu-(D)-Trp-(D)Ala-βAla-Tyr-(D)Phe-OH.

TLC: 0.09 (Rf2) HPLC eluting time: 22.8 minutes Mass analysis: $(M+H)^+=864.4$

EXAMPLE 58

Production of 2-Thienyl—CO—Leu-(D)Trp-(D)Ala-βAla-Tyr-(D)Phe—OH

Using 2-thiophenecarbonyl chloride in place of adamantan-1-ylcarbonyl chloride in the production in Example 19, the same procedure as in Example 19 was followed to yield 87 mg of a white powder of 2-thienyl—CO—Leu-(D)Trp-(D)Ala-βAla-Tyr-(D)Phe—OH.
TLC: 0.10 (Rf2)
HPLC eluting time: 23.4 minutes
Mass analysis: $(M+H)^+=880.3$

EXAMPLE 59

Production of Quinoxalin-2-yl—CO—Leu-(D)Trp-(D)Ala-βAla-Tyr-(D)Phe—OH

Using 2-quinoxaloyl chloride in place of adamantan-1-ylcarbonyl chloride in the production in Example 19, the same procedure as in Example 19 was followed to yield 59 mg of a white powder of quinoxalin-2-yl—CO—Leu-(D)Trp-(D)Ala-βAla-Tyr-(D)Phe—OH.
Mass analysis: $(M+H)^+=927.4$

EXAMPLE 60

Production of Benzoyl-Leu-(D)Trp-(D)Ala-βAla-Tyr-(D)Phe—OH

Using benzoyl chloride in place of adamantan-1-ylcarbonyl chloride in the production in Example 19, the same procedure as in Example 19 was followed to yield 124 mg of a white powder of benzoyl-Leu-(D)Trp-(D)Ala-βAla-Tyr-(D)Phe—OH.
Mass analysis: $(M+H)^+=874.4$

EXAMPLE 61

Production of Ph$_2$N—CO—Leu-(D)Trp-(D) Ala-βAla-Tyr-(D)Phe—OH

Using diphenylcarbamoyl chloride in place of adamantan-1-ylcarbonyl chloride in the production in Example 19, the same procedure as in Example 19 was followed to yield 34 mg of a white powder of Ph$_2$N—CO—Leu-(D)Trp-(D)Ala-βAla-Tyr-(D)Phe—OH.
TLC: 0.14 (Rf2)
HPLC eluting time: 26.6 minutes
Mass analysis: $(M+H)^+=965.5$

EXAMPLE 62

Production of PhNH—CO—Leu-(D)Trp-(D)Ala-βAla-Tyr-(D)Phe—OH

Using phenyl isocyanate in place of adamantan-1-ylcarbonyl chloride in the production in Example 19, the same procedure as in Example 19 was followed to yield 39 mg of a white powder of PhNH—CO—Leu-(D)Trp-(D)Ala-βAla-Tyr-(D)Phe—OH.
Mass analysis: $(M+H)^+=889.5$

EXAMPLE 63

Production of Tetrahydronaphthalene—CO—Leu-(D)Trp-(D)Ala-βAla-Tyr-(D)Phe—OH

Boc-Leu-(D) Trp-(D)Ala-βAla-Tyr-(D)Phe-OBzl (0.1 g) was dissolved in 4N hydrochloric acid/ethyl acetate (1 ml), and the resulting solution was kept standing at room temperature for 30 minutes. After the solvent was distilled off under reduced pressure, the residue was filtered with diethyl ether and dried, after which it was dissolved in N,N-dimethylformamide (1 ml). After this solution was neutralized with triethylamine (15 µl), 1,2,3,4-tetrahydro-2-naphthoic acid (17 mg), HOBt (15 mg) and WSCD.HCl (22 mg) were added, followed by stirring at room temperature overnight. The mixture was treated in the same manner as in Example 19 to yield 37 mg of a white powder of tetrahydronaphthalene—CO—Leu-(D)Trp-(D)Ala-βAla-Tyr-(D)Phe—OH.
TLC: 0.15 (Rf2)
HPLC eluting time: 25.5 minutes
Mass analysis: $(M+H)^+=928.5$

EXAMPLE 64

Production of 2, 2-Dimethylbutyryl-Leu-(D)Trp-(D)Ala-βAla-Tyr-(D)Phe—OH

Using 2,2-dimethylbutyric acid in place of 1,2,3,4-tetrahydro-2-naphthoic acid in the production in Example 63, the same procedure as in Example 63 was followed to yield 33 mg of a white powder of 2,2-dimethylbutyryl-Leu-(D)Trp-(D)Ala-βAla-Tyr-(D)Phe—OH.
TLC: 0.19 (Rf2)
HPLC eluting time: 24.6 minutes
Mass analysis: $(M+H)^+=868$

EXAMPLE 65

Production of Hexamethyleneimino—CO—Leu-(D)Trp-(D)Pya(2)-βAla-Tyr-(D)Phe—OH

Using Boc-(D)Pya(2)—OH in place of Boc-(D)Ala—OH in the production in Example 39, the same procedure as in Example 39 was followed to yield 21 mg of a white powder of hexamethyleneimino—CO—Leu-(D)Trp-(D)Pya(2)-βAla-Tyr-(D)Phe—OH.
TLC: 0.07 (Rf2)
HPLC eluting time: 23.1 minutes
Mass analysis: $(M+H)^+=972.4$

EXAMPLE 66

Production of Hexamethyleneimino—CO—Leu-(D)Trp-(D)Pya(3)-βAla-Tyr-(D)Phe—OH

Using Boc-(D)Pya(3)—OH in place of Boc-(D)Ala—OH in the production in Example 39, the same procedure as in Example 39 was followed to yield 27 mg of a white powder of hexamethyleneimino—CO—Leu-(D)Trp-(D)Pya(3)-βAla-Tyr-(D)Phe—OH.
TLC: 0.07 (Rf2)
HPLC eluting time: 23.1 minutes
Mass analysis: $(M+H)^+=927.4$

EXAMPLE 67

Production of Hexamethyleneimino—CO—Leu-(D)Trp(Me)-(D)Ala-βAla-Tyr-(D)Phe—OH

Using Boc-(D)Trp(Me)—OH in place of Boc-(D)Trp—OH in the production in Example 39, the same procedure as in Example 39 was followed to yield 58 mg of a white powder of hexamethyleneimino—CO—Leu-(D)Trp(Me)-(D)Ala-βAla-Tyr-(D)Phe—OH.
TLC: 0.22 (Rf2)
HPLC eluting time: 24.7 minutes
Mass analysis: $(M+H)^+=909.4$

EXAMPLE 68

Production of Hexamethyleneimino—CO—Leu-(D)Trp(Me)-(D)Pya(2)-βAla-Tyr-(D)Phe—OH

Using Boc-(D)Trp(Me)—OH and Boc-(D)Pya(2)—OH in place of Boc-(D)Trp—OH and Boc-(D)Ala—OH, respectively, in the production in Example 39, the same procedure as in Example 39 was followed to yield 28 mg of a white powder of hexamethyleneimino—CO—Leu-(D) Trp(Me)-(D)Pya(2)-βAla-Tyr-(D)Phe—OH.
TLC: 0.18 (Rf2)
HPLC eluting time: 24.5 minutes
Mass analysis: $(M+H)^+=986.4$

EXAMPLE 69

Production of Boc-Leu-(D)Trp(Me)-(D)Ala-βAla-Tyr-(D)Phe—OH

Using Boc-(D)Trp(me)—OH in place of Boc-(D) Trp—OH in the production in Example 1, the same procedure as in Example 1 was followed to yield 39 mg of a white powder of Boc-Leu-(D)Trp(Me)-(D) Ala-βAla-Tyr-(D)Phe—OH.
TLC: 0.27 (Rf2)
HPLC eluting time: 25.8 minutes
Mass analysis: $(M+H)^+=884$

EXAMPLE 70

Production of Boc-Leu-(D)Trp-(D)Pya(2)-βAla-Tyr-(D)Phe—OH

Using Boc-(D)Pya(2)—OH in lace of Boc-(D)Ala—OH in the production in Example 1, the same procedure as in Example 1 was followed to yield 59 mg of a white powder of Boc-Leu-(D)Trp-(D)Pya(2)-βAla-Tyr-(D)Phe—OH.
TLC: 0.07 (Rf2)
HPLC eluting time: 23.4 minutes
Mass analysis: $(M+H)^{+=947.4}$

EXAMPLE 71

Production of Boc-Leu-(D)Trp-(D)Pya(3)-βAla-Tyr-(D)Phe—OH

Using Boc-(D)Pya(3)—OH in place of Boc-(D)Ala—OH in the production in Example 1, the same procedure as in Example 1 was followed to yield 43 mg of a white powder of Boc-Leu-(D)Trp-(D)Pya(3)-βAla-Tyr-(D)Phe—OH.
TLC: 0.07 (Rf2)
HPLC eluting time: 23.4 minutes
Mass analysis: $(M+H)^+=947.4$

EXAMPLE 72

Production of Boc-Leu-(D)Trp-(D)Ala-βAla-Trp—NH—Ind—OH

Using Boc-Trp-OH and H—NH—Ind—OCH$_3$.HCl in place of Boc-Tyr—OH and H-(D)Phe-OBzl.HCl, respectively, in the production in Example 1, the same procedure as in Example 1 was followed to yield Boc-Leu-(D)Trp-(D)Ala-βAla-Trp—NH—Ind—OCH$_3$, which was subjected to the same ester hydrolysis and purification procedures as in Example 64 to yield 75 mg of a white powder of Boc-Leu-(D)Trp-(D) Ala-βAla-Trp—NH—Ind—OH.
TLC: 0.26 (Rf2), 0.67 (Rf3)
HPLC eluting time: 26.2 minutes
Mass analysis: $(M+H)^+=905.4$

EXAMPLE 73

Production of Boc-Leu-(D)Trp-(D)Ala-βAla-Trp-(D)Trp—OH

Using H-(D)Trp—OCH$_3$.HCl in place of H-(D)Phe-OBzl.HCl in the production in Example 1, the same procedure as in Example 1 was followed to yield Boc-Leu-(D)Trp-(D)Ala-βAla-Trp-(D) Trp—OCH$_3$, which was subjected to the same ester hydrolysis and purification procedures as in Example 43 to yield 75 mg of a white powder of Boc-Leu-(D)Trp-(D)Ala-βAla-Trp-(D)Trp—OH.
TLC: 0.14 (RF2)

HPCL eluting time: 26.0 minutes
Mass analysis: (M+H)⁺=932

EXAMPLE 74

Production of Boc-Leu-(D)Trp-(D)Ala-βAla-Tyr-(Bzl)-(D)Trp—OH

Using Boc-Trp—OH in place of Boc-Tyr—OH in the production in Example 73, the same procedure as in Example 43 was followed to yield 75 mg of a white powder of Boc-Leu-(D)Trp-(D)Ala-βAla-Tyr(Bzl)-(D)Trp—OH.
TLC: 0.43 (Rf2)
HPLC eluting time: 27.0 minutes
Mass analysis: (M+H)⁺=999.6

EXAMPLE 75

Production of Boc-Leu-(D)Trp-(D)Ala-βAla-Tyr-Iqu—OH

Using Boc-Iqu—OH and H-(D)Trp—OCH₃.HCl in place of Boc-Tyr—OH and H-(D)Phe-OBzl.HCl, respectively, in the production in Example 1, the same procedure as in Example 1 was followed to yield Boc-Leu-(D)Trp-(D)Ala-βAla-Tyr-Iqu—OCH₃, which was subjected to the same ester hydrolysis and purification procedures as in Example 43 to yield 27 mg of a white powder of Boc-Leu-(D)Trp-(D)Ala-βAla-Tyr-Iqu—OH.
TLC: 0.38 (Rf2)
HPLC eluting time: 22.5 minutes
Mass analysis: (M+H)⁺=882.4

EXAMPLE 76

Production of Cyclohexyl—CO—Leu-(D)Trp-(D)Ala-βAla-Tyr-(D)Phe—OH

Using cyclohexanecarbonyl chloride in place of adamantan-1-ylcarbonyl chloride in the production in Example 19, the same procedure as in Example 19 was followed to yield 40 mg of a white powder of cyclohexyl—CO—Leu-(D)Trp-(D) Ala-βAla-Tyr-(D)Phe—OH.
TLC: 0.19 (Rf2)
HPLC eluting time: 24.3 minutes
Mass analysis: (M+H)⁺=880

EXAMPLE 77

Production of Cycloheptyl—CO—Leu-(D)Trp-(D)Ala-βAla-Tyr-(D)Phe—OH

Using cycloheptanecarboxylic acid in place of 1,2,3,4-tetrahydro-2-naphthoic acid in the production in Example 63, the same procedure as in Example 63 was followed to yield 23 mg of a white powder of cycloheptyl—CO—Leu-(D)Trp-(D)Ala-βAla-Tyr-(D)Phe—OH.
TLC: 0.20 (Rf2)
HPLC eluting time: 25.2 minutes
Mass analysis: (M+H)⁺=894

EXAMPLE 78

Production of Boc-Leu-(D)Trp-(D)Ala-(D)Glu(Tyr-(D)Phe)—OCH₃

Using Boc-(D)Glu—OCH₃ in place of Boc-βAla—OH in the production in Example 1, the same procedure as in Example 1 was followed to yield 61 mg of a white powder of Boc-Leu-(D)Trp-(D)Ala-(D)Glu(Tyr-(D)Phe)—OCH₃.
TLC: 0.30 (Rf2)
HPLC eluting time: 24.8 minutes
Mass analysis: (M+H)⁺=942.5

EXAMPLE 79

Production of Boc-Leu-(D)Trp-(D) Ala-(D)Glu(Tyr-(D)Phe)—OH

The compound of Example 78 was subjected to the same ester hydrolysis and purification procedures as in Example 43 to yield 21 mg of a white powder of Boc-Leu-(D)Trp-(D)Ala-(D)Glu(Tyr-(D)Phe)—OH.
TLC: 0.25 (Rf3)
HPLC eluting time: 23.7 minutes
Mass analysis: (M+H)⁺=928.5

EXAMPLE 80

Using the corresponding dipeptide of Examples 2 to 4 respectively in place of Boc-Tyr-(D)Phe-OBzl in the production in Example 70, the same procedure as in Example 1 was followed to yield the following compounds 80-1 through 80-3.

80-1: Boc-Leu-(D)Trp-(D)Pya(2)-βAla-Tyr-Phe—OH 80-2: Boc-Leu-(D)Trp-(D)Pya(2)-βAla-(D)Tyr-(D)Phe—OH 80-3: Boc-Leu-(D)Trp-(D)Pya(2)-βAla-(D)Tyr-Phe—OH

EXAMPLE 81

Using the corresponding dipeptide of Examples 2 to 4 respectively in place of Boc-Tyr-(D)Phe-OBzl in the production in Example 71, the same procedure as in Example 1 was followed to yield the following compounds 81-1 through 81-3.

81-1: Boc-Leu-(D)Trp-(D)Pya(3)-βAla-Tyr-Phe—OH 81-2: Boc-Leu-(D)Trp-(D)Pya(3)-βAla-(D)Tyr-(D)Phe—OH 81-3: Boc-Leu-(D)Trp-(D)Pya(3)-βAla-(D)Tyr-Phe—OH

EXAMPLE 82

Using the corresponding dipeptide of Examples 2 to 4 respectively in place of Boc-Tyr-(D)Phe-OBzl in the production in Example 69, the same procedure as in Example 1 was followed to yield the following compounds 82-3 through 82-4.

82-1: Boc-Leu-(D)Trp(Me)-(D)Ala-Tyr-Phe—OH 82-2: Boc-Leu-(D)Trp(Me)-(D)Ala-βAla-(D)Tyr-(D)Phe—OH 82-3: Boc-Leu-(D)Trp(Me)-(D)Ala-βAla-(D)Tyr-Phe—OH

EXAMPLE 83

Using the corresponding dipeptide of Examples 2 to 4 respectively in place of Boc-Tyr-(D)Phe-OBzl in the production in Example 57, the same procedure as Example 1 was followed to yield the following compounds 83-1 through 83-3.

83-1: 2-furyl—CO—Leu-(D)Trp-(D)Ala-βAla-Tyr-Phe—OH 83-2: 2-furyl—CO—Leu-(D)Trp-(D)Ala-βAla-(D)Tyr-(D)Phe—OH 83-3: 2-furyl—CO—Leu-(D)Trp-(D)Ala-βAla-(D)Tyr-Phe—OH

EXAMPLE 84

Using the corresponding dipeptide of Examples 2 to 4 respectively in place of Boc-Tyr-(D)Phe-OBzl in the production in Examples 58, the same procedure as in Example 19 was followed to yield the following compounds 84-1 through 84-3.

84-1: 2-thienyl—CO—Leu-(D)Trp-(D)Ala-βAla-Tyr-Phe—OH 84-2: 2-thienyl—CO—Leu-(D)Trp-(D)Ala-βAla-(D)Tyr-(D)Phe—OH 84-3: 2-thienyl—CO—Leu-(D)Trp-(D)Ala-βAla-(D)Tyr-Phe—OH

EXAMPLE 85

Using the corresponding dipeptide of Examples 2 to 4 respectively in place of Boc-Tyr-(D)Phe-OBzl in the production in Examples 59, the same procedure as in Example 19 was followed to yield the following compounds 85-1 through 85-3.

85-1: Quinoxalin-2-yl—CO—Leu-(D)Trp-(D)Ala-βAla-Tyr-Phe—OH 85-2: Quinoxalin-2-yl—CO—Leu-(D)Trp-(D)Ala-βAla-(D)Tyr-(D)Phe—OH 85-3: Quinoxalin-2-yl—CO—Leu-(D)Trp-(D)Ala-βAla-(D)Tyr-Phe—OH

EXAMPLE 86

Using the corresponding dipeptide of Examples 2 to 4 respectively in place of Boc-Tyr-(D)Phe-OBzl in the production in Examples 60, the same procedure as in Example 19 was followed to yield the following compounds 86-1 through 86-3.

86-1: Ph—CO—Leu-(D)Trp-(D)Ala-βAla-Tyr-Phe—OH 86-2: Ph—CO—Leu-(D)Trp-(D)Ala-βAla-(D)Tyr-(D)Phe—OH 86-3: Ph—CO—Leu-(D)Trp-(D)Ala-βAla-(D)Tyr-Phe—OH

EXAMPLE 87

Using 10,11-Dihydro-5H-dibenz(b,f)azepine-5-carbonyl chloride in place of Adamantan-1-ylcarbonyl chloride in the production in Examples 19 and 20, the same procedure as in Example 19 was followed to yield the following compounds 87-1 and 87-2. Also, using Boc-(D)Tyr—OH in place of Boc-Tyr—OH in the production of compounds 87-1 and 87-2, the same procedure as in Example 19 was followed to yield the following compounds 87-3 and 87-4.

87-1: Dba—CO—Leu-(D)Trp-(D)Ala-βAla-Tyr-(D)Phe—OH 87-2: Dba—CO—Leu-(D)Trp-(D)Ala-βAla-Tyr-Phe—OH 87-3: Dba—CO—Leu-(D)Trp-(D)Ala-βAla-(D)Tyr-(D)Phe—OH 87-4: Dba—CO—Leu-(D)Trp-(D)Ala-βAla-(D)Tyr-Phe—OH

EXAMPLE 88

Using the corresponding dipeptide of Examples 3 and 4 respectively in place of Boc-Tyr-(D)Phe-OBzl in the production of compound 39, the same procedure as in Example 39 was followed to yield the following compounds 88-1 and 88-2.

88-1: Hexamethylenimino-CO-(D)Trp-(D)Ala-βAla-(D)Tyr-(D)Phe—OH 88-2: Hexamethylenimino—CO—Leu-(D)Trp-(D)Ala-βAla-(D)Tyr-Phe—OH

EXAMPLE 89

Using the corresponding dipeptide of Examples 2 to 4 respectively in place of Boc-Tyr-(D)Phe-OBzl and in the production of compounds 68, the same procedure as in Example 39 was followed to yield the following compounds 89-1 through 89-3.

89-1: Hexamethylenimino—CO—Leu-(D)Trp(Me)-Pya(2)-βAla-Tyr-Phe—OH 89-2: Hexamethylenimino—CO—Leu-(D)Trp(Me)-Pya(2)-βAla-(D)Tyr-(D)Phe—OH 89-3: Hexamethylenimino—CO—Leu-(D)Trp(Me)-Pya(2)-βAla-(D)Tyr-Phe—OH

EXAMPLE 90

Using the corresponding dipeptide of Examples 2 to 4 respectively in place of Boc-Tyr-(D)Phe-OBzl in the production of compound 67, the same procedure as in Example 39 was followed to yield the following compounds 90-1 through 90-3.

90-1: Hexamethylenimino—CO—Leu-(D)Trp(Me)-(D)Ala-βAla-Tyr-Phe—OH 90-2: Hexamethylenimino—CO—Leu-(D)Trp(Me)-(D)Ala-βAla-(D)Tyr-(D)Phe—OH 90-3: Hexamethylenimino—CO—Leu-(D)Trp(Me)-(D)Ala-βAla-(D)Tyr-Phe—OH

EXAMPLE 91

Using Boc-(D)Tyr-OBzl, Boc-Tyr-OBzl, Boc-(D)Phe-OBzl or Boc-Phe-OBzl in place of Boc-Tyr-(D)Phe-OBzl in the production of compound 62, the same procedure as in Example 62 was followed to yield the following compounds 91-1through 91-4.

92-1: PhNH—CO—Leu-(D)Trp-(D)Ala-βAla-(D)Tyr—OH 92-2: PhNH—CO—Leu-(D)Trp-(D)Ala-βAla-Tyr—OH 92-3: PhNH—CO—Leu-(D)Trp-(D)Ala-βAla-(D)Phe—OH 92-4: PhNH—CO—Leu-(D)Trp-(D)Ala-βAla-Phe—OH

EXAMPLE 92

Using Boc-Glu(OBzl)-OPac, Boc-Glu(OPac)-OBzl, Boc-(D)Asp(OBzl)-OPac or Boc-(D)Asp(OPac)-OBzl in place of Boc-Tyr-(D)Phe-OBz in the production in compound 56, the same procedure as in Example 56 was followed to yield the following compounds 92-1 through 92-4.

93-1: PhCH$_2$NH—CO—Leu-(D)Trp-(D)Ala-βAla-Glu-(OBzl)—OH 93-2: PhCH$_2$NH—CO—Leu-(D)Trp-(D) Ala-βAla-Glu-OBzl 93-3: PhCH$_2$NH—CO—Leu-(D)Trp-(D)Ala-βAla-(D)Asp(OBzl)—OH 93-4: PhCH$_2$NH—CO—Leu-(D)Trp-(D)Ala-βAla-(D)Asp-OBzl

EXAMPLE 93

Using the corresponding dipeptide of Examples 2 to 4 respectively in place of Boc-Tyr-(D)Phe—OBzl in the production of compound 53, the same procedure as in Example 39 was followed to yield the following compounds 93-1through 93-3.

93-1: (Cyclohexyl)$_2$N—CO—Leu-(D)Trp-(D)Ala-βAla-Tyr-Phe—OH 93-2: (Cyclohexyl)$_2$N—CO—Leu-(D)Trp-(D)Ala-βAla-(D)Tyr-(D)Phe—OH 93-3: (Cyclohexyl)$_2$N—CO—Leu-(D)Trp-(D)Ala-βAla-(D)Tyr-Phe—OH

EXAMPLE 94

Using the corresponding dipeptide of Examples 2 to 4 respectively in place of Boc-Tyr-(D)Phe-OBzl in the production of compounds 52, the same procedure as in Example 19 was followed to yield the following compounds 94-1 through 94-3.

94-1: Cyclohexyl—NH—CO—Leu-(D)Trp-(D)Ala-βAla-Tyr-Phe—OH 94-2: Cyclohexyl—NH—CO—Leu-(D)Trp-(D)Ala-βAla-(D)Tyr-(D)Phe—OH 94-3: Cyclohexyl—NH—CO—Leu-(D)Trp-(D)Ala-βAla-(D)Tyr-Phe—OH

EXAMPLE 95

Using the corresponding dipeptide of Examples 2 to 4 respectively in place of Boc-Tyr-(D)Phe-OBzl in the production of compound 61, the same procedure as in Example 19 was followed to yield the following compounds 95-1 through 95-3.

95-1: Ph$_2$N—CO—Leu-(D)Trp-(D)Ala-βAla-Tyr-Phe—OH 95-2: Ph$_2$N—CO—Leu-(D)Trp-(D)Ala-βAla-(D)Tyr-(D)Phe—OH 95-3: Ph$_2$N—CO—Leu-(D)Trp-(D)Ala-βAla-(D)Tyr-Phe—OH

EXAMPLE 96

Using the corresponding dipeptide of Examples 2 to 4 respectively in place of Boc-Tyr-(D)Phe-OBzl in the production of compound 64, the same procedure as in Example 1 was followed to yield the following compounds 96-1through 96-3.

96-1: 2,2-dimethylbutyryl-Leu-(D)Trp-(D)Ala-βAla-Tyr-Phe—OH 96-2: 2,2-dimethylbutyryl-Leu-(D)Trp-(D)Ala-βAla-(D)Tyr-(D)Phe—OH 96-3: 2,2-dimethylbutyryl-Leu-(D)Trp-(D)Ala-βAla-(D)Tyr-Phe—OH

EXAMPLE 97

Using the corresponding dipeptide of Examples 2 to 4 respectively in place of Boc-Tyr-(D)Phe-OBzl in the production of compound 76, the same procedure as in Example 19 was followed to yield the following compounds 97-1 through 97-3.

97-1: Cyclohexyl—CO—Leu-(D)Trp-(D)Ala-βAla-Tyr-Phe—OH 97-2: Cyclohexyl—CO—Leu-(D)Trp-(D)Ala-βAla-(D)Tyr-(D)Phe—OH 97-3: Cyclohexyl—CO—Leu-(D)Trp-(D)Ala-βAla-(D)Tyr-Phe—OH

EXAMPLE 98

Using the corresponding dipeptide of Examples 2 to 4 respectively in place of Boc-Tyr-(D)Phe-OBzl in the production of compound 63, the same procedure as in Example 63 was followed to yield the following compounds 98-1through 98-3.

98-1: Tna—CO—Leu-(D)Trp-(D)Ala-βAla-Tyr-Phe—OH 98-2: Tna—CO—Leu-(D)Trp-(D)Ala-βAla-(D)Tyr-(D)Phe—OH 98-3: Tna—CO—Leu-(D)Trp-(D)Ala-βAla-(D)Tyr-Phe—OH

REFERENCE EXAMPLE 1

Production of Boc-Leu-(D)Trp-(D)Ala-βAla-Glu—OH

Using Boc-Glu(OBzl)-OBzl in place of Boc-Tyr-(D)Phe-OBzl in the production in Example 1, the same procedure as in Example 1 was followed to yield 150 mg of a white powder of Boc-Leu-(D)Trp-(D)Ala-βAla-Glu—OH.
TLC (Rf2) 0.12, HPLC eluting time 20.9 minutes
Mass analysis: (M+H)$^+$=689.6

REFERENCE EXAMPLE 2

Production of Boc-Leu-(D)Trp-(D)Ala-βAla-(D)Leu—OH

Using Boc-(D)Leu-OBzl in place of Boc-Tyr-(D)Phe-OBzl in the production in Example 1, the same procedure as in Example 1 was followed to yield 134 mg of a white powder of Boc-Leu-(D) Trp-(D) Ala-βAla-(D)Leu—OH.
TLC (Rf2) 0.48, HPLC eluting time 24.0 minutes
Mass analysis: (M+H)$^+$=673.3

TEST EXAMPLE

Receptor Binding Assay

The membrane fraction prepared from swine heart was diluted to 0.15 mg/ml with an assaying buffer and dispensed to assaying tubes at 100 μl per tube. To this membrane fraction suspension were added 2 μl of a solution of endothelin-1labeled with 5 nM radioactive iodine and 3 μl of a 50% dimethylsulfoxide solution of the subject peptide, followed by incubation at 25° C. After 1 hour, the suspension was diluted with 900 μl of an ice-cooled assaying buffer and centrifuged at 12,000×G for 10 minutes to separate supernatant and precipitate. The precipitate contained cell membranes and endothelin receptors embedded therein. The receptor-bound endothelin, labeled with radioactive iodine, was also recovered in the precipitate. The radioactive iodine in this precipitate was counted, using a gamma ray counter, to determine the amount of radioactive-iodine-labeled endothelin bound to the endothelin receptors. The results of the quantitative determination are shown in IC$_{50}$ (M) below.

| | |
|---|---|
| Compound of Example 1 | $4.6 \times 10^{-9}$ |
| Compound of Example 2 | $9.0 \times 10^{-9}$ |
| Compound of Example 5 | $7.2 \times 10^{-9}$ |
| Compound of Example 38 | $6.0 \times 10^{-8}$ |
| Compound of Example 39 | $3.4 \times 10^{-10}$ |
| Compound of Example 43 | $7.1 \times 10^{-10}$ |
| Compound of Reference Example 1 | $7.0 \times 10^{-7}$ |
| Compound of Reference Example 2 | $4.2 \times 10^{-7}$ |

The above result shows that peptides having an aromatic cycle of this invention have an more excellent endothelin receptor-antagonistic activity compared with peptides having no aromatic cycles.

We claim:

1. A peptide having the formula:

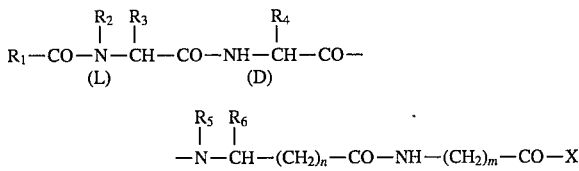

wherein $R_1$ is (1) a straight or branched $C_{1-10}$ alkyl group optionally substituted with 1 to 3 substituents selected from the group consisting of $C_{3-8}$ cycloalkyl groups, halogen atoms, $C_{1-6}$ alkoxy groups, $C_{1-6}$ alkylthio groups, $C_{1-6}$ alkoxycarbonyl groups, and 5- to 10-membered aromatic heterocyclic groups;

(2) a $C_{3-10}$ cycloalkyl optionally substituted with 1 to 3 substituents selected from the group consisting of $C_{1-6}$ alkyl groups, halogen atoms, $C_{1-6}$ alkoxy groups, $C_{1-6}$ alkylthio groups, and $C_{1-6}$ alkoxycarbonyl groups, or the cycloalkyl group condensed with another ring;

(3) a straight or branched $C_{1-8}$ alkoxy group optionally substituted with 1 to 3 substituents selected from the group consisting of $C_{3-8}$ cycloalkyl groups, $C_{1-6}$ alkoxy groups and $C_{1-6}$ alkoxycarbonyl groups;

(4) a $C_{6-15}$ aromatic hydrocarbon group optionally substituted with 1 to 3 substituents selected from the group consisting of halogen atoms, hydroxy groups, $C_{1-6}$ alkyl groups, $C_{1-6}$ alkoxy groups, carboxyl groups, $C_{1-6}$ alkylcarbonyl groups and $C_{1-6}$ alkoxycarbonyl groups:

(5) a 5- to 6-membered aromatic heterocyclic group having 1 to 4 hetero atoms selected from O, S and N or the aromatic heterocyclic group condensed with an aromatic ring, optionally substituted with 1to 3 substituents selected from the group consisting of halogen atoms, hydroxy groups, $C_{1-6}$ alkyl groups, $C_{1-6}$ alkoxy groups, carboxyl groups, $C_{1-6}$ alkylcarbonyl groups and $C_{1-6}$ alkoxycarbonyl groups; or (6) an amino group having the formula $R_7NH-$ or $R_8R_9N-$ wherein each of $R_7$, $R_8$ and $R_9$ independently is (i) a $C_{4-10}$ alkyl group optionally substituted with 1 to 3 substituents selected from the group consisting of $C_{3-8}$ cycloalkyl groups, $C_{1-6}$ alkoxy groups, $C_{1-6}$ alkylthio groups, hydroxy groups, carboxyl groups, $C_{1-6}$ alkylcarbonyl groups, 5- to 10-membered aromatic heterocyclic groups having 1 to 4 hetero atoms selected from O, S and N, and $C_{6-12}$ aromatic hydrocarbon groups optionally substituted with a halogen atom, a hydroxy group, a $C_{1-3}$ alkoxy group or a $C_{1-3}$ alkyl group;

(ii) a $C_{5-10}$ cycloalkyl group optionally substituted with 1 to 3 substituents selected from the group consisting of $C_{1-6}$ alkyl groups, $C_{1-6}$ alkoxy groups, $C_{1-6}$ alkylthio groups, hydroxy groups, carboxyl groups and $C_{1-6}$ alkylcarbonyl groups;

(iii) a $C_{6-12}$ aromatic hydrocarbon group optionally substituted with 1 to 3 substituents selected from the group consisting of $C_{1-6}$ alkyl groups, $C_{1-6}$ alkoxy groups, hydroxy groups, carboxyl groups and $C_{1-6}$ alkylcarbonyl groups; or (iv) a 5- to 10-membered aromatic heterocyclic group having 1 to 4 hetero atoms selected from O, N and S or the aromatic heterocyclic group condensed with an aromatic ring, optionally substituted with 1 to 3 substituents selected from the group consisting of $C_{1-6}$ alkyl groups, $C_{1-6}$ alkoxy groups, hydroxy groups, carboxyl groups, $C_{1-6}$ alkylcarbonyl groups and nitrogen atoms optionally substituted with 1 to 3 $C_{1-6}$ alkyl groups;

or $R_8$ and $R_9$ together form a 5- to 13-membered nitrogen-containing heterocyclic ring optionally having 1 or 2 hetero atoms selected from O and S atoms, the said 5- to 13-membered nitrogen-containing heterocyclic ring optionally substituted with 1 to 3 substituents selected form the group consisting of $C_{1-6}$ alkyl groups, phenyl groups, halogen atoms, nitro groups, cyano groups, hydroxy groups, $C_{1-4}$ alkoxy groups, $C_{1-4}$ alkylthio groups, amino groups, mono- and di-$C_{1-4}$ alkylamino groups, $C_{1-4}$ alkylcarbonylamino groups, $C_{1-4}$ alkylsulfonylamino groups, $C_{1-4}$ alkoxycarbonyl groups, carboxyl groups, $C_{1-6}$ alkylcarbonyl groups, $C_{1-4}$ alkylcarbonyloxy groups and 5- to 6-membered heterocyclic groups having 1 to 4 hetero atoms selected from O, S and N;

$R_2$ and $R_5$ independently are a hydrogen atom or a lower alkyl group;

$R_3$ is a $C_{1-8}$ alkyl, $C_{3-8}$ cycloalkyl, or $C_{3-8}$ cycloalkyl group substituted with a $C_{1-8}$ alkyl group, optionally including an oxygen or sulfur atom between adjacent methylene groups;

$R_4$ is a heterocyclic-substituted $C_{1-6}$ alkyl group, wherein the heterocyclic substituent is a 5- or 6-membered heterocyclic group having 1 to 4 hetero atoms selected from O, S and N, or the heterocyclic group is condensed with another ring, and the carbon atoms of the heterocyclic-substituted $C_{1-6}$ alkyl group are optionally substituted with 1 to 3 substituents selected from the group consisting of $C_{1-6}$ alkyl groups, halogen atoms, hydroxyl groups, carboxyl groups, $C_{1-6}$ alkoxy groups, and $C_{1-6}$ alkylcarbonyl groups, and nitrogen atoms of the heterocyclic-substituted $C_{1-6}$ alkyl group are optionally substituted with 1 to 3 substituents selected from the group consisting of $C_{1-6}$ alkyl groups, $C_{1-6}$ alkylcarbonyl groups and hydroxy-$C_{1-6}$ alkyl groups;

$R_6$ is (A) a hydrogen atom;

(B) a straight or branched $C_{1-6}$ alkyl group optionally substituted with 1 to 3 substituents selected from the group consisting of (i) $C_{6-15}$ aromatic hydrocarbon groups, (ii) 5- to 6-membered aromatic heterocyclic groups having 1 to 4 hetero atoms selected from O, S and N or the heterocyclic group is condensed with an aromatic ring, (iii) sulfur-containing groups selected from thione, mercapto, methylthio, ethylthio and phenylthio groups, (iv) oxygen-containing groups selected from ketone, hydroxy, methoxy, ethoxy, phenoxy and benzyloxy groups and (v) nitrogen-containing groups selected from amino, N-methylamino, N-ethylamino and guanidino groups;

(C) a $C_{6-12}$ aromatic hydrocarbon group optionally substituted with 1 to 3 substituents selected from the group consisting of $C_{1-6}$ alkyl groups, halogen atoms, $C_{1-6}$ alkoxy groups, $C_{1-6}$ alkylthio groups, $C_{1-6}$ alkylcarbonyl groups and $C_{1-6}$ alkoxycarbonyl groups; or (D) a 5- to 6-membered aromatic heterocyclic group which contains 1 to 4 hetero atoms selected from O, S and N or the heterocyclic group is condensed with another ring optionally substituted with 1 to 3 substituents selected from the group consisting of $C_{1-6}$ alkyl groups, halogen atoms, $C_{1-6}$ alkoxy groups, $C_{1-6}$ alkylthio groups, $C_{1-6}$ alkylcarbonyl groups and $C_{1-6}$ alkoxycarbonyl groups;

X is (i) a group resulting from the elimination of one hydrogen atom from the α-amino group of an α-amino acid having at least one cyclic group selected from the group consisting of (a) $C_{6-15}$ aromatic hydrocarbon groups optionally substituted with 1 to 3 substituents selected from the group consisting of halogen atoms, hydroxy groups, $C_{1-6}$ alkyl groups, $C_{1-6}$ alkoxy groups, carboxyl groups, $C_{1-6}$ alkylcarbonyl groups, and $C_{1-6}$ alkoxycarbonyl groups, and (b) 5- to 6-membered aromatic heterocyclic groups having 1 to 4 hetero atoms selected from O, S and N or the heterocyclic group is condensed with an aromatic ring optionally substituted with 1 to 3 substituents selected from the group consisting of halogen atoms, hydroxy groups, $C_{1-6}$ alkyl groups, $C_{1-6}$ alkoxy groups, carboxyl groups, $C_{1-6}$ alkylcarbonyl groups and $C_{1-6}$ alkoxycarbonyl groups; or (ii) alkylamino groups substituted with an aromatic group wherein the alkylamino groups are $C_{1-10}$ alkylamino groups or $C_{3-10}$ cycloalkylamino groups;

n is 0 or an integer of 1 to 4;

m is an integer of 2 to 6; or a salt thereof.

2. The peptide as claimed in claim 1 wherein $R_8$ and $R_9$ together form pyrrolidinyl, piperidinyl, hexamethyleneiminyl, heptamethyleneiminyl, oxazolidinyl, morphonyl, thiazolidinyl, thiomorphonyl, imidazolidinyl, piperazinyl, pyrrolyl, 1,2-dihydropyridinyl, 1-4-dihydropyridinyl, 1,2,3,6-tetrahydropyridinyl, 2-oxazolidonyl 2-thiazolidonyl, imidazolyl, 1,4,5,6-tetrahydropyrimidihyl, 2,3,4,5-tetrahydro-1H-indolyl, 1,2,3,4-tetrahydroquinolinyl, 2,3,4,5-tetrahydro-1H-1-benzazepinyl, 2,3-dihydro-1H-isoindolyl, 1,2,3,4-tetrahydroisoquinolyl, 2,3,4,5-tetrahydro-1H-2-benzazepinyl, 2,3,4,5-tetrahydro-1H-3-benzazepinyl, 1,2,3,4,5,6-hexahydro-1-benzazocinyl, 1,2,3,4,5,6-hexahydro-2-benzazocinyl, 1,2,3,4,5,6-hexahydro-3-benzazocinyl, 2,3,4,5,6,7-hexahydro-1H-1-benzazonyl, 2,3,4,5,6,7-hexahydro-1H-2-benzazonyl, 2,3,4,5,6,7-hexahydro-1H-3-benzazonyl, 2,3,4,5,6,7-hexahydro-1H-4-benzazonyl, β-carbolynyl, phenothiadinyl, 3H-3-benzazepinyl, 3,4-dihydroquinolyl, benzimidanyl, 1,4-benzodiazepinyl or 10, 11-dihydro-5H-dibenz (b,f) azepine-5-yl.

3. The peptide as claimed in claim 1 wherein $R_3$ is methoxymethyl, ethoxymethyl, 2-methoxyethyl, 2-ethoxyethyl, 3-methoxypropyl, 3-ethoxypropyl, methylthiomethyl, ethylthiomethyl, 2-methylthioethyl, 2-ethylthioethyl, 3-methylthiopropyl or 3-ethylthiopropyl group.

4. The peptide as claimed in claim 1 wherein $R_3$ is a tetrahydrofuran-2-yl or tetrahydrothiophen-2-yl group.

5. The peptide as claimed in claim 1 wherein $R_3$ is a cyclopenthlthiomethyl or cyclohexylthiomethyl group.

6. The peptide as claimed in claim 1 wherein $R_6$ is a furyl, thienyl, pyridyl, thiazolyl, imidazolyl or indolyl.

7. The peptide as claimed in claim 1 wherein X is a 2-furyl, 3-furyl, 2-thienyl, 3-thienyl, thiazol-4-yl, 2-pyridyl, 3-pyridyl, 4-pyridyl, 2-pyranyl, indol-3-yl, N-methylindol-3-yl, 2-quinolyl or quinoxalin-2-yl group.

8. The peptide of claim 1, selected from the group consisting of Boc-Leu-(D)Trp-(D)Ala-βAla-Tyr-(D)Phe—OH, Boc-Leu-(D)Trp-(D)Ala-βAla-Tyr-Phe—OH, Boc-Leu-(D)Trp-(D)Ala-βAla-(D)Tyr-(D)Phe—OH, Boc-Leu-(D)Trp-(D)Ala-βAla-(D)Tyr-Phe—OH, Boc-Leu-(D)Trp-(D)Ala-εAhx-Tyr-Phe—OH, Boc-Leu-(D)Trp-(D)Trp-(D)Ala-βAla-Tyr-Phe—OH, Boc-Leu-(D)Trp-(D)Ala-βAla-(D)Tyr—OH, Boc-Leu-(D)Trp-(D)Ala-βAla-Tyr—OH, Boc-Leu-(D)Trp-(D)Ala-βAla-(D)Phe—OH, Boc-Leu-(D)Trp-(D)Ala-βAla-Phe—OH, Boc-Leu-(D)Trp-(D)Ala-βAla-(D)(m-F)Tyr—OH, Boc-Leu-(D)Trp-(D)Ala-βAla-(m-F)Tyr—OH, Boc-Leu-(D)Trp-(D)Ala-βAla-(D)(p-F)Phe—OH, Boc-Leu-(D)Trp-(D)Ala-βAla-(p-F)Phe—OH, Boc-Leu-(D)Trp-(D)Ala-βAla-(D)Phg—OH, Boc-Leu-(D)Trp-(D)Trp-(D)Ala-βAla-Trp—OH, Boc-Leu-(D)Trp-(D)Ala-βAla-Tyr-(D)Trp-OH, Boc-Leu-(D)Trp-(D)Ala-βAla-Trp-(D)Phe—OH, Adamantan-1-ylcarbonyl-Leu-(D)Trp-(D)Ala-βAla-Tyr-(D)Phe—OH, Adamantan-1-ylcarbonyl-Leu-(D)Trp-(D)Ala-βAla-Tyr-Phe—OH, (1S)-(−)-Camphanyl-Leu-(D)Trp-(D)Ala-βAla-Tyr-(D)Phe—OH, Boc-Leu-(D)Trp-(D)Ala-βAla-Glu(OBzl)—OH, Boc-Leu-(D)Trp-(D)Ala-βAla-Glu-OBzl, Boc-Leu-(D)Trp-(D)Ala-βAla-(D)Asp(OBzl)—OH, Boc-Leu-(D)Trp-(D)Ala-βAla-(D)Asp-OBzl, Boc-Leu-(D)Trp-(D)Ala-βAla-Glu—NHCHPhCH$_2$Ph, Boc-Leu-(D)-Trp-(D)Ala-εAhx-Glu—NHCH$_2$CHPh$_2$, Boc-Leu-(D)Trp-(D)Ala-εAhx-Asp—NHCHPhCH$_2$Ph, Boc-Leu-(D)Trp-(D)Ala-βAla-Asp—NHCH$_2$CHPh$_2$, Boc-Leu-(D)Trp-(D)Ala-βAla-Asp—NHCH$_2$CH$_2$-Ind, Boc-Leu-(D)Trp-(D)Ala-βAla-Asp(NHCH$_2$CH$_2$-Ind), Boc-Leu-(D)Trp-(D)Ala-βAla-Glu-Asp(NBzl$_2$)—NHCHCH$_2$-Ind, Boc-Leu-(D)Trp-βAla-Glu-Asp(NHCH$_2$CH$_2$-Ind)-NBzl$_2$, Boc-Leu-(D)Trp-(D)Ala-βAla-Asp-NBzl$_2$, Boc-Leu-(D)Trp-(D)Ala-GABA-Tyr-Phe—OH, Boc-Leu-(D)Trp-(D)Ala-εAhx—NHCHPhCH$_2$PH, Boc-Leu-(D)Trp-(D)Ala-εAhx—NHCH$_2$CHPh$_2$, Boc-Leu-(D)Trp-(D) Ala-βAla-(m-F)Tyr-(p-F)Phe—OH, Hexamethyleneimino—CO—Leu-(D)Trp-(D)Ala-βAla-(m-F)Tyr-(p-F)Phe—OH, Hexamethyleneimino—CO—Leu-(D)Trp-(D)Ala-βAla-Tyr-(D)Phe—ONa, Hexamethyleneimino—CO—Leu-(D)Trp-(D)Ala-βAla-Tyr-Phe—OH, Hexamethyleneimino—CO—Leu-(D)Trp-Ala-βAla-Tyr-(D)Phe—OH, Hexamethyleneimino—CO—Leu-(D)Trp-(D)Ala-βAla-Tyr(I)-(D)Phe—OH, Hexamethyleneimino—CO—Leu-(D)Trp-(D)Thg(2)-βAla-Tyr-(D)Phe—OH, Hexamethyleneimino—CO—Leu-(D)Trp-(D)Thg(3)-βAla-Tyr-(D)Phe—OH, Hexamethyleneimino—CO—Leu-(D)Trp-(D)Thi-βAla-Tyr-(D)Phe—OH, Hexamethyleneimino—CO—Leu-(D)Trp-(D)Ala-βAla-Tyr-(D)Phe-εAhx—OH, Hexamethyleneimino—CO—Leu-(D)Trp-(D)Ala-βAla-Tyr-(D)Phe-βAla—OH, Hexamethyleneimino—CO—Leu-(D)Trp-(D)Ala-βAla-Trp—NH—Ind—OH, Hexamethyleneimino—CO—Leu-(D)Trp-(D)Ala-βAla-Iqu-(D)Trp—OH, Hexamethyleneimino—CO—Leu-(D)Trp-(D)His-βAla-Tyr-(D)Phe—OH, Cyclohexyl—NH—CO—Leu-(D)Trp-(D)Ala-βAla-Tyr-(D)Phe—OH, Dicyclohexyl—NH—CO—Leu-(D)Trp-(D)Ala-βAla-Tyr-(D)Phe—OH, Me-Pip—CO—Leu-(D)Trp-(D)Ala-βAla-Tyr-(D)Phe—OH, Pym-Pip—CO—Leu-(D)Trp-(D)Ala-βAla-Tyr-(D)Phe—OH, PhCH$_2$NH—CO—Leu-(D)Trp-(D)Ala-βAla-Tyr-(D)Phe—OH, 2-Furyl—CO—Leu-(D)Trp-(D)Ala-βAla-Tyr-(D)Phe—OH, 2-Thienyl—CO—Leu-(D)Trp-(D)Ala-βAla-Tyr-(D)Phe—OH, Quinoxalin-2-yl—CO—

Leu-(D)Trp-(D)Ala-βAla-Tyr-(D)Phe—OH, Benzoyl-Leu-(D)Trp-(D)Ala-βAla-Tyr-(D)Phe—OH, Ph₂N—CO—Leu-(D)Trp-(D)Ala-βAla-Tyr-(D)Phe—OH, PhNH—CO—Leu-(D)Trp-(D)Ala-βAla-Tyr-(D)Phe—OH, Tetrahydronaphthalene—CO—Leu-(D)Trp-(D)Ala-βAla-Tyr-(D)Phe—OH, 2, 2-Dimethylbutyryl-Leu-(D)Trp-(D)Ala-βAla-Tyr-(D)Phe—OH, Hexamethyleneimino—CO—Leu-(D)Trp-(D)Pya(2)-βAla-Tyr-(D)Phe—OH, Hexamethyleneimino—CO—Leu-(D)Trp-(D)Pya(3)-βAla-Tyr-(D)Phe—OH, Hexamethyleneimino—CO—Leu-(D)Trp(Me)-(D)Ala-βAla-Tyr-(D)Phe—OH, Hexamethyleneimino—CO—Leu-(D)Trp(Me)-(D)Pya(2)-βAla-Tyr-(D)Phe—OH, Boc-Leu-(D)Trp(Me)-(D)Ala-βAla-Tyr-(D)Phe—OH, Boc-Leu-(D)Trp-(D)Pya(2)-βAla-Tyr-(D)Phe—OH, Boc-Leu-(D)Trp-(D)Pya(3)-βAla-Tyr-(D)Phe—OH, Boc-Leu-(D)Trp-(D)Ala-βAla-Trp—NH—Ind—OH, Boc-Leu-(D)Trp-(D)Ala-βAla-Trp-(D)Trp—OH, Boc-Leu-(D)Trp-(D)Ala-βAla-Tyr-(Bzl)-(D)Trp—OH, Boc-Leu-(D)Trp-(D)Ala-βAla-Tyr-Iqu—OH, Cyclohexyl—CO—Leu-(D)Trp-(D)Ala-βAla-Tyr-(D)Phe—OH, Cycloheptyl—CO—Leu-(D)Trp-(D)Ala-βAla-Tyr-(D)Phe—OH, Boc-Leu-(D)Trp-(D)Ala-(D)Glu(Tyr-(D)Phe)—OCH₃, Boc-Leu-(D)Trp-(D)Ala-(D)Glu(Tyr-(D)Phe)—OH, Boc-Leu-(D)Trp-(D)Pya(2)-βAla-Tyr-Phe—OH, Boc-Leu-(D)Trp-(D)Pya(2)-βAla-(D)Tyr-(D)Phe—OH, Boc-Leu-(D)Trp-(D)Pya(2)-βAla-(D)Tyr-Phe—OH, Boc-Leu-(D)Trp-(D)Pya(3)-βAla-Tyr-Phe—OH, Boc-Leu-(D)Trp-(D)Pya(3)-βAla-(D)Tyr-(D)Phe—OH, Boc-Leu-(D)Trp-(D)Pya(3)-βAla-(D)Tyr-Phe—OH, Boc-Leu-(D)Trp(Me)-(D)Ala-βAla-Tyr-Phe—OH, Boc-Leu-(D)Trp(Me)-(D)Trp(Me)-(D)Ala-βAla-(D)Tyr-(D)Phe—OH, Boc-Leu-(D)Trp(Me)-(D)Ala-βAla-(D)Tyr-Phe—OH, 2-furyl—CO—Leu-(D)Trp-(D)Ala-βAla-Tyr-Phe—OH, 2-furyl—CO—Leu-(D)Trp-(D)Ala-βAla-(D)Tyr-(D)Phe—OH, 2-furyl—CO—Leu-(D)Trp-(D)Ala-βAla-(D)Tyr-Phe—OH, 2-thienyl—CO—Leu-(D)Trp-(D)Ala-βAla-Tyr-Phe—OH, 2-thienyl—CO—Leu-(D)Trp-(D)Ala-βAla-(D)Tyr-(D)Phe—OH, 2-thienyl—CO—Leu-(D)Trp-(D)Ala-βAla-(D)Tyr-Phe—OH, Quinoxalin-2-yl—CO—Leu-(D)Trp-(D)Ala-βAla-Tyr-Phe—OH, Quinoxalin-2-yl—CO—Leu-(D)Trp-(D)Ala-βAla-(D)Tyr-(D)Phe—OH, Quinoxalin-2-yl—CO—Leu-(D)Trp-(D)Ala-βAla-(D)Tyr-Phe—OH, Ph—CO—Leu-(D)Trp-(D)Ala-βAla-Tyr-Phe—OH, Ph—CO—Leu-(D)Trp-(D)Ala-βAla-(D)Tyr-(D)Phe—OH, Ph—CO—Leu-(D)Trp-(D)Ala-βAla-(D)Tyr-Phe—OH, Dba—CO—Leu-(D)Trp-(D)Ala-βAla-Tyr-(D)Phe—OH, Dba—CO—Leu-(D)Trp-(D)Ala-βAla-Tyr-Phe—OH, Dba-CO-Leu-(D)Trp-(D)Ala-βAla-(D)Tyr-(D)Phe—OH, Dba—CO—Leu-(D)Trp-(D)Ala-βAla-(D)Tyr-Phe—OH, Hexamethyleneimino—CO—Leu-(D)Trp-(D)Ala-βAla-Tyr-(D)Phe—OH, Hexamethyleneimino—CO—Leu-(D)Trp-(D)Ala-βAla-(D)Try-Phe—OH, Hexamethyleneimino—CO—Leu-(D)Trp(Me)-Pya(2)-βAla-Tyr-Phe—OH, Hexamethyleneimino—CO—Leu-(D)Trp(Me)-Pya(2)-βAla-(D)Tyr-(D)Phe—OH, Hexamethyleneimino—CO—Leu-(D)Trp(Me)-Pya(2)-βAla-(D)Tyr-Phe—OH, Hexamethyleneimino—CO—Leu-(D)Trp(Me)-(D)Ala-βAla-Tyr-Phe—OH, Hexamethyleneimino—CO—Leu-(D)Trp(Me)-(D)Ala-βAla-Tyr-(D)Phe—OH, Hexamethyleneimino—CO—Leu-(D)Trp(Me)-(D)Ala-βAla-Tyr-Phe—OH, PhNH—CO—Leu-(D)Trp-(D)Ala-βAla-Tyr—OH, PhNH—CO—Leu-(D)Trp-(D)Ala-βAla-Tyr—OH, PhNH—CO—Leu-(D)Trp-(D)Ala-βAla-(D)Phe—OH, PhNH—CO—Leu-(D)Trp-(D) Ala-βAla-Phe—OH, PhCH₂NH—CO—Leu-(D)Trp-(D)Ala-βAla-Glu(OBzl)—OH, PhCH₂NH—CO—Leu-(D)Trp-(D)Ala-βAla-Glu-OBzl, PhCH₂NH—CO—Leu-(D)Trp-(D)Ala-βAla-(D)Asp(OBzl)—OH, PhCH₂NH—CO—Leu-(D)Trp-(D)Ala-βAla-(D)Asp-OBzl, (Cyclohexyl)₂N—CO—Leu-(D)Trp-(D)Ala-βAla-Tyr-Phe—OH, (Cyclohexyl)₂N—CO—Leu-(D)Trp-(D)Ala-βAla-(D)Tyr-(D)Phe—OH, (Cyclohexyl)₂N—CO—Leu-(D)Trp-(D)Ala-βAla-(D)Tyr-Phe—OH, Cyclohexyl—NH—CO—Leu-(D)Trp-(D)Ala-βAla-Tyr-Phe—OH, Cyclohexyl—NH—CO—Leu-(D)Trp-(D)Ala-βAla-(D)Tyr-(D)Phe—OH, Cyclohexyl—NH—CO—Leu-(D)Trp-(D)Ala-βAla-(D)Tyr-Phe—OH, Ph₂N—CO—Leu-(D)Trp-(D)Ala-βAla-Tyr-Phe—OH, Ph₂N—CO—Leu-(D)Trp-(D)Ala-βAla-(D)Tyr-(D)Phe—OH, Ph₂N—CO—Leu-(D)Trp-(D)Ala-βAla-(D)Tyr-Phe—OH, 2,2-dimethylbutyryl-Leu-(D)Trp-(D)Ala-βAla-Tyr-Phe—OH, 2,2-dimethylbutyryl-Leu-(D)Trp-(D)Ala-βAla-(D)Tyr-(D)Phe—OH, 2,2-dimethylbutyryl-Leu-(D)Trp-(D)Ala-βAla-(D)Tyr-Phe—OH, Cyclohexyl—CO—Leu-(D)Trp-(D)Ala-βAla-Tyr-Phe—OH, Cyclohexyl—CO—Leu-(D)Trp-(D)Ala-βAla-(D)Tyr-(D)Phe—OH, Cyclohexyl—CO—Leu-(D)Trp-(D)Ala-βAla-(D)Tyr-Phe—OH, Tna—CO—Leu-(D)Trp-(D)Ala-βAla-(D)Tyr-Phe—OH, Tna—CO—Leu-(D)Trp-(D)Ala-βAla-(D)Tyr-(D)Phe—OH, and Tna—CO—Leu-(D)Trp-(D)Ala-βAla-(D)Tyr-Phe—OH.

9. The peptide of claim 1, selected from the group consisting of Boc-Leu-(D)Trp-(D)Ala-βAla-(D)Tyr-(D)Phe—OH, Boc-Leu-(D)Trp-(D)Ala-βAla-(D)Tyr-Phe—OH, Boc-Leu-(D)Trp-(D)Trp-βAla-Tyr-Phe—OH, Boc-Leu-(D)Trp-(D)Ala-βAla-(D)Tyr—OH, Boc-Leu-(D)Trp-(D)Ala-βAla-Tyr—OH, Boc-Leu-(D)Trp-(D)Ala-βAla-(D)Phe—OH, Boc-Leu-(D)Trp-(D)Ala-βAla-Phe—OH, Boc-Leu-(D)Trp-(D)Ala-βAla-(D)(m-F)Tyr—OH, Boc-Leu-(D)Trp-(D)Ala-βAla-(p-F)Phe—OH, Boc-Leu-(D)Trp-(D)Ala-βAla-(D)Phg—OH, Boc-Leu-(D)Trp-(D)Ala-βAla-Trp—OH, Boc-Leu-(D)Trp-(D)Ala-βAla-Tyr-(D)Trp—OH, Boc-Leu-(D)Trp-(D)Ala-βAla-Trp-(D)Phe—OH, Adamantan-1-ylcarbonyl-Leu-(D)Trp-(D)Trp-(D)Ala-βAla-Tyr-(D)Phe—OH, (1S)-(−)-Camphanyl-Leu-(D)Trp-(D)Ala-βAla-Tyr-(D)Phe—OH, Boc-Leu-(D)Trp-(D)Ala-βAla-Glu(OBzl)—OH, Boc-Leu-(D)Trp-(D)Ala-βAla-Glu-OBzl, Boc-Leu-(D)Trp-(D)Ala-βAla-Glu—NHCHPhCH₂Ph, Boc-Leu-(D)Trp-(D)Ala-εAhx-Asp—NHCHPhCH₂Ph, Boc-Leu-(D)Trp-(D)Ala-βAla-Asp—NHCH₂CH₂-Ind, Boc-Leu-(D)Trp-(D)Ala-βAla-Asp-NBzl₂, Boc-Leu-(D)Trp-(D)Ala-GABA-Tyr-Phe—OH, Hexamethyleneimino—CO—Leu-(D)Trp-(D)Ala-βAla-Tyr-(D)Phe—ONa, Hexamethyleneimino—CO—Leu-(D)Trp-(D)Ala-βAla-Tyr-Phe—OH, Hexamethyleneimino—CO—Leu-(D)Trp-Ala-βAla-Tyr-(D)Phe—OH, Hexamethyleneimino—CO—Leu-(D)Trp-(D)Thg(2)-βAla-Tyr-(D)Phe—OH, Hexamethyleneimino—CO—Leu-(D)Trp-(D)Thg(3)-βAla-Tyr-(D)Phe—OH, Hexamethyleneimino—CO—Leu-(D)Trp-(D)Thi-βAla-Tyr-(D)Phe—OH, Hexamethyleneimino—CO—Leu-(D)Trp-(D)Ala-βAla-Tyr-(D)Phe-εAhx—OH, Hexamethyleneimino—CO—Leu-(D)Trp-(D)Ala-βAla-Tyr-(D)Phe-βAla—OH, Hexamethyleneimino—CO—Leu-(D)Trp-(D)Ala-βAla-Trp—NH—Ind—OH, Hexamethyleneimino—CO—Leu-(D)Trp-(D)Ala-βAla-Iqu-(D)Trp—OH, Hexamethyleneimino—CO—Leu-(D)Trp-(D)His-βAla-Tyr-(D)Phe—OH, Cyclohexyl—NH—CO—Leu-(D)Trp-(D)Ala-βAla-Tyr-(D)Phe—OH, Dicyclohexyl—NH—CO—Leu-(D)Trp-(D)Ala-βAla-Tyr-(D)Phe—OH, Me-Pip—CO—Leu-(D)Trp-(D)Ala-βAla-Tyr-(D)Phe—OH, Pym-Pip—CO—Leu-(D)Trp-(D)Ala-βAla-Tyr-(D)Phe—OH, PhCH₂NH—CO—Leu-(D)Trp-(D)Ala-βAla-Tyr-(D)Phe—OH, 2-Furyl—CO—Leu-(D)Trp-(D)Ala-βAla-Tyr-(D)Phe—OH, 2-Thienyl—CO—Leu-(D)Trp-(D)Ala-βAla-Tyr-(D)Phe—OH, Quinoxalin-2-yl—CO—Leu-(D)Trp-(D)Ala- βAla-Tyr-(D)Phe—OH, Benzoyl-Leu-(D)Trp-(D)Ala-βAla-Tyr-(D)Phe—OH, Ph$_2$N—CO—Leu-(D)Trp-(D)Ala-βAla-Tyr-(D)Phe—OH, PhNH—CO—Leu-(D)Trp-(D)Ala-βAla-Tyr-(D)Phe—OH, Tetrahydronaphthalene—CO—Leu-(D)Trp-(D)Ala-βAla-Tyr-(D)Phe—OH, 2,2-Dimethylbutryryl-Leu-(D)Trp-(D)Ala-βAla-Tyr-(D)Phe—OH, Hexamethyleneimino—CO—Leu-(D)Trp-(D)Pya(2)-βAla-Tyr-(D)Phe—OH, Hexamethyleneimino—CO—Leu-(D)Trp-(D)Pya(3)-βAla-Tyr-(D)Phe—OH, Hexamethyleneimino—CO—Leu-(D)Trp(Me)-(D)Ala-βAla-Tyr-(D)Phe—OH, Hexamethyleneimino—CO—Leu-(D)Trp(Me)-(D)Pya(2)-βAla-Tyr-(D)Phe—OH, Boc-Leu-(D)Trp(Me)-(D)Ala-βAla-Tyr-(D)Phe—OH, Boc-Leu-(D)Trp-(D)Pya(2)-βAla-Tyr-(D)Phe—OH, Boc-Leu-(D)Trp-(D)Pya(3)-βAla-Tyr-(D)Phe—OH, Boc-Leu-(D)Trp-(D)Ala-βAla-Trp—NH—Ind—OH, Boc-Leu-(D)Trp-(D)Ala-βAla-Trp-(D)Trp—OH, Boc-Leu-(D)Trp-(D)Ala-βAla-Tyr-(Bzl)-(D)Trp—OH, Boc-Leu-(D)Trp-(D)Ala-βAla-Tyr-Iqu—OH, Cyclohexyl—CO—Leu-(D)Trp-(D)Ala-βAla-Tyr-(D)Phe—OH, Cycloheptyl—CO—Leu-(D)Trp-(D)Ala-βAla-Tyr-(D)Phe—OH, Boc-Leu-(D)Trp-(D)Ala-(D)Glu(Tyr-(D)Phe)—OCH$_3$, Boc-Leu-(D)Trp-(D)Pya(2)-βAla-(D)Tyr-Phe—OH, Boc-Leu-(D)Trp(Me)-(D)Ala-βAla-(D)Tyr-Phe—OH, 2-furyl—CO—Leu-(D)Trp-(D)Ala-βAla-Tyr-Phe—OH, 2-thienyl—CO—Leu-(D)Trp-(D)Ala-βAla-(D)Tyr-Phe—OH, Quinoxalin-2-yl—CO—Leu-(D)Trp-(D)Ala-βAla-(D)Tyr-(D)Phe—OH, Ph—CO—Leu-(D)Trp-(D)Ala-βAla-(D)Tyr-Phe—OH, Hexamethyleneimino—CO—Leu-(D)Trp-(D)Ala-βAla-(D)Tyr-(D)Phe—OH, Hexamethyleneimino—CO—Leu-(D)Trp-(D)Ala-βAla-Try-Phe—OH, Hexamethyleneimino—CO—Leu-(D)Trp(Me)-Pya(2)-βAla-(D)Tyr-(D)Phe—OH, Hexamethyleneimino—CO—Leu-(D)Trp(Me)-(D)Ala-βAla-(D)Tyr-Phe—OH, PhNH—CO—Leu-(D)Trp-(D)Ala-βAla-Tyr—OH, PhCH$_2$NH—CO—Leu-(D)Trp-(D)Ala-βAla-Glu(OBzl)—OH, PhCH$_2$NH—CO—Leu-(D)Trp-(D)Ala-βAla-Glu-OBzl, PhCH$_2$NH—CO—Leu-(D)Trp-(D)Ala-βAla-(D)Asp(OBzl)—OH, PhCH$_2$NH—CO—Leu-(D)Trp-(D)Ala-βAla-(D)Asp-OBzl, Cyclohexyl—NH—CO—Leu-(D)Trp-(D)Ala-βAla-(D)Tyr-Phe—OH, 2,2-dimethylbutyryl-Leu-(D)Trp-(D)Ala-βAla-(D)Tyr-Phe—OH, and Cyclohexyl—CO—Leu-(D)Trp-(D)Ala-βAla-(D)Tyr-Phe—OH.

10. The peptide as claimed in claim 1 wherein $R_1$ is a straight or branched $C_{1-10}$ alkyl, $C_{3-10}$ cycloalkyl, $C_{1-8}$ alkoxy, phenyl, naphthyl, phenyl-$C_{1-10}$ alkyl, indan-1-yl, indan-2-yl, 1,2,3,4-tetrahydronaphthalene-1-yl, 1,2,3,4-tetrahydronaphthalene-2-yl, 2-furyl, 3-furyl, 2-thienyl, 3-thienyl, thiazol-4-yl, 2-pyridyl, 4-pyridyl, 2-pyranyl, indol-3-yl, N-methylindol-3-yl, 2-quinolyl, quinoxalin-2-yl, mono- or di-phenylamino, phenyl-$C_{1-10}$ alkyl amino, methylpiperazino or 1-(2-pyrimidyl)piperazino, $R_2$ is a hydrogen atom or a straight or branched $C_{1-6}$ alkyl group, $R_3$ is a $C_{1-6}$ alkyl group, $R_4$ is a 2-pyridyl-$C_{1-6}$ alkyl, imidazol-2-yl-$C_{1-6}$ alkyl, imidazol-4-yl-$C_{1-6}$ alkyl, indol-3-yl-$C_{1-6}$ alkyl, N-methylindol-3-yl-$C_{1-6}$ alkyl, N-ethylindol-3-yl-$C_{1-6}$ alkyl, N-hydroxymethylindol-3-yl-$C_{1-6}$ alkyl, N-formylindol-3-yl-$C_{1-6}$ alkyl, thiazol-4-yl-$C_{1-6}$ alkyl or 5-fluoroindol-3-yl-$C_{1-6}$ alkyl group, $R_5$ is a hydrogen atom or a $C_{1-6}$ alkyl group, $R_6$ is a $C_{1-6}$ alkyl, furyl, thienyl, pyridyl, pyridyl-$C_{1-6}$ alkyl or indolyl-$C_{1-6}$ alkyl group, X is -Tyr—OH, -Phe—OH, -Trp—OH, -Phg—OH, -Tyr-Phe—OH, -Try-Trp—OH, -Tyr-Trp—OH, -Trp-Trp—OH, -(m-F)Tyr—OH, -(P-F)Phe—OH, -(m-F)Tyr-(p-F)Phe—OH, -(I)Tyr-Phe—OH, -Tyr(Bzl)-Phe—OH, -Trp(Bzl)-Trp—OH, -(I)Tyr-Trp—OH, -(I)Tyr-Tyr—OH, -Glu(Obzl)—OH, -Glu-OBzl, -Asp(OBzl)—OH, -Asp-OBzl, -Glu—NHCHPhCH$_2$Ph, -Glu—NHCH$_2$CHPh$_2$, -Asp—NHCHPhCH$_2$Ph, -Asp—NHCH$_2$CHPh$_2$, -Asp—NHCH$_2$CH$_2$-Ind, -Asp-(NHCH$_2$CH$_2$-Ind)—OH, -Glu-Asp—NHCH$_2$CH$_2$-Ind, -Glu-Asp(NHCH$_2$CH$_2$-Ind)-NBzl$_2$, -Asp-NBzl$_2$, -Trp—NH—Ind or -Trp-Iqu, n is 0, and m is an integer of 2 to 6.

11. The peptide as claimed in claim 1 wherein $R_1$ is a straight or branched $C_{1-10}$ alkyl, $C_{3-10}$ cycloalkyl, $C_{1-8}$ alkoxy, phenyl, naphthyl, phenyl-$C_{1-10}$ alkyl, indan-1-yl, indan-2-yl, 1,2,3,4-tetrahydronaphthalene-1-yl,1,2,3,4-tetrahydronaphthalene-2-yl, 2-furyl, 3-furyl, 2-thienyl, 3-thienyl, thiazol-4-yl, 2-pyridyl, 4-pyridyl, 2-pyranyl, indol-3-yl, N-methylindol-3-yl, 2-quinolyl, quinoxalin-2-yl, mono- or di-phenylamino, phenyl-$C_{1-10}$ alkyl amino, methylpiperazino or 1-(2-pyrimidyl)piperazino, $R_2$ is a hydrogen atom, $R_3$ is a $C_{1-6}$ alkyl group, $R_4$ is a indol-3-yl-$C_{1-6}$ alkyl or N-methylindol-3-yl-$C_{1-6}$ alkyl group, $R_5$ is a hydrogen atom, $R_6$ is a $C_{1-6}$ alkyl, furyl, thienyl, pyridyl, pyridyl-$C_{1-6}$ alkyl or indolyl-$C_{1-6}$ alkyl group, X is -Tyr—OH, -Phe—OH, -Trp—OH, -Phg—OH, -Tyr-Phe—OH, -Tyr-Trp-OH, -Try-Trp—OH, -Trp-Trp-OH, -(m-F)Tyr—OH, -(P-F)Phe—OH, -(m-F)Tyr-(p-F)Phe—OH, -(I)Tyr-Phe—OH, -Tyr(Bzl)-Phe—OH, -Trp(Bzl)-Trp—OH, -(I)Tyr-Tyr—OH, -Glu(OBzl)—OH, -Glu-OBzl, -Asp(OBzl)—OH, -Asp-Obzl, -Glu—NHCHPhCH$_2$Ph, -Glu—NHCH$_2$CHPh$_2$, -Asp—NHCHPhCH$_2$PH, -Asp—NHCH$_2$CHPh$_2$, -Asp—NHCH$_2$CH$_2$-Ind, -Asp-(NHCH$_2$CH$_2$-Ind)—OH, -Glu-Asp—NHCH$_2$CH$_2$-Ind, -Glu-Asp(NHCH$_2$CH$_2$-Ind)-NBzl$_2$, -Asp-NBzl$_2$, -Trp—NH—Ind or -Trp-Iqu, n is 0, and m is an integer of 2 to 6.

12. The peptide as claimed in claim 1 wherein $R_1$ is a straight or branched $C_{1-10}$ alkyl, $C_{3-10}$ cycloalkyl, $C_{1-8}$ alkoxy, phenyl, naphthyl, phenyl-$C_{1-10}$ alkyl, indan-1-yl, indan-2-yl, 1,2,3,4-tetrahydronaphthalene-1-yl, 1,2,3,4-tetrahydronaphthalene-2-yl, 2-furyl, 3-furyl, 2-thienyl, 3-thienyl, thiazol-4-yl , 2-pyridyl, 4-pyridyl, 2-pyranyl, indol-3-yl, N-methylindol-3-yl, 2-quinolyl, quinoxalin-2-yl, mono- or di-phenylamino, phenyl-$C_{1-10}$ alkyl amino, methylpiperazino or 1-(2-pyrimidyl)piperazino, $R_2$ is a hydrogen atom, $R_3$ is a $C_{1-6}$ alkyl group, $R_4$ is a indol-3-yl-$C_{1-6}$ alkyl or N-methylindol-3-yl-$C_{1-6}$ alkyl group, X is -Tyr—OH, -Phe—OH, -Trp—OH, -Phg—OH, -Tyr-Phe—OH, -Tyr-Trp—OH, -Tyr-Trp—OH, -Trp-Trp—OH, -(m-F)Tyr—OH, -(P-F)Phe—OH, -(m-F)Tyr-(p-F)Phe—OH, -(I)Tyr-phe—OH, -Tyr(Bzl)-Phe—OH, -Trp(Bzl)-Trp—OH, -(I)Tyr-Trp—OH, -(D)Tyr-Tyr—OH, -Tyr(Bzl)-Phe—OH, -Glu-OBzl, -Asp(OBzl)—OH, -Asp-Obzl, -Glu—NHCHPhCH$_2$PH, -Glu—NHCH$_2$CHPh$_2$, -Asp—NHCHPhCH$_2$Ph, -Asp—NHCH$_2$CHPh$_2$, -Asp—NHCH$_2$CH$_2$—Ind, -Asp-(NHCH$_2$CH$_2$—Ind)—OH, -Glu-Asp—NHCH$_2$CH$_2$—Ind, -Glu-Asp(NHCH$_2$CH$_2$—Ind)-NBzl$_2$, -Asp-NBzl$_2$, -Trp—NH—Ind or -Trp-Iqu, n is 0, the —N(R$_5$)—(HCR$_6$)—(CH$_2$)n—CO— moiety is an α-amino acid residue selected from the group consisting of Ala, Val, Leu, Ile, Trp, Pya(2) and Pya(3), and m is an integer of 2 to 6.

13. A method of treating hypertension in a mammal, which comprises administering an effective amount of the peptide or a pharmacologically acceptable salt thereof as claimed in claim 1 to the mammal.

14. The peptide as claimed in claim 1 wherein the ring formed by R$_8$ and R$_9$ is a hexamethyleneiminyl, 10,11-dihydro-5H-dibenz (b,f) azepin-5-yl, morpholinyl, piperidinyl, methylpiperazinyl or 1-(2-pyrimidyl)piperazinyl.

15. The peptide as claimed in claim 1 wherein the 5- or 6-membered heterocyclic group which contains 1 to 4 hetero atoms of O, S and N or the group as condensed with another aromatic ring of R$_1$ is a 2-furyl, 3-furyl, 2-thienyl, 3-thienyl, thiazol-4-yl, 2-pyridyl, 3-pyridyl, 4-pyridyl, 2-pyranyl, indol-3-yl, N-methylindol-3-yl, 2-quinolyl or quinoxalin-2-yl.

16. The peptide as claimed in claim 1 wherein R$_1$ is a straight or branched C$_{1-10}$ alkyl, C$_{3-10}$ cycloalkyl, C$_{1-8}$ alkoxy, phenyl, naphthyl, phenyl-C$_{1-10}$ alkyl, indan-1-yl, indan-2-yl, 1,2,3,4-tetrahydronaphthalene-1-yl, 1,2,3,4-tetrahydronaphthalene-2-yl, 2-furyl, 3-furyl, 2-thienyl, 3-thienyl, thiazol-4-yl, 2-pyridyl, 4-pyridyl, 2-pyranyl, indol-3-yl, N-methylindol-3-yl, 2-quinolyl, quinoxalin-2-yl, mono- or di-phenylamino, phenyl-C$_{1-10}$ alkyl amino, methylpiperazino or 1-(2-pyrimidyl)piperazino.

17. The peptide as claimed in claim 1 wherein R$_2$ is a hydrogen atom or a straight or branched C$_{1-6}$ alkyl group.

18. The peptide as claimed in claim 1 wherein R$_2$ is a hydrogen atom.

19. The peptide as claimed in claim 1 wherein R$_3$ is a C$_{1-6}$ alkyl group.

20. The peptide as claimed in claim 1 wherein R$_4$ is a 2-pyridyl-C$_{1-6}$ alkyl, imidazol-2-yl-C$_{1-6}$ alkyl, imidazol-4-yl-C$_{1-6}$ alkyl, indol-3-yl-C$_{1-6}$ alkyl, N-methylindol-3-yl-C$_{1-6}$ alkyl, N-ethylindol-3-yl-C$_{1-6}$ alkyl, N-hydroxymethylindol-3-yl-C$_{1-6}$ alkyl, N-formylindol-3-yl-C$_{1-6}$ alkyl, thiazol-4-yl-C$_{1-6}$ alkyl or 5-fluoroindol-3-yl-C$_{1-6}$ alkyl group.

21. The peptide as claimed in claim 1 wherein R$_4$ is a indol-3-yl-C$_{1-6}$ alkyl or N-methylindol-3-yl-C$_{1-6}$ alkyl group.

22. The peptide as claimed in claim 1 wherein R$_5$ is a hydrogen atom or a C$_{1-6}$ alkyl group.

23. The peptide as claimed in claim 1 wherein R$_5$ is a hydrogen atom.

24. The peptide as claimed in claim 1 wherein R$_6$ is a C$_{1-6}$ alkyl, furyl, thienyl, pyridyl, pyridyl-C$_{1-6}$ alkyl or indolyl-C$_{1-6}$ alkyl group.

25. The peptide as claimed in claim 1 wherein the α-amino acid is Gly, Ala, Val, Leu, Ile, Ser, Thr, Glu, Asn, Phe, Trp, Met, His, Cys, Arg, Asn, Gln, Tyr, (I)Tyr, diiodo-Tyr, Phg, Cha, Nva, Nle, Rya(2), Pya(3) or Thi which is optionally substituted or protected at a 1-carboxyl group thereof by (i) an ester selected from the group consisting of a benzyl ester, diphenylmethyl ester and trityl ester or (ii) an amide selected from the group consisting of a phenylamide, benzylamide, diphenylamide, dibenzylamide, 2-phenylethylamide, 2,2-diphenylethylamide, 1,2-diphenylethylamide and indol-3-yl-methylamide.

26. The peptide as claimed in claim 1 wherein X is the group resulting from elimination of one hydrogen atom from the α-amino group of α-amino acid having at least one aromatic cyclic group is a group selected from the group consisting of Phe—OH, -Tyr—OH, -Trp—OH, -Phg—OH, -(m-F)Tyr—OH, -(p-F)Phe—OH, -(p—Cl)Phe—OH, -(p-Me)Phe—OH, -Trp(Me)—OH, -Trp(CHO)—OH, -Phe-Trp—OH, -Trp-Phe—OH, -Tyr-Trp—OH, -Trp-Phe—OH, -(m-F)Tyr-(p-F)Phe—OH, -Glu(OBzl)—OH, -Glu-OBzl, -Asp(OBzl)—OH, -Asp-OBzl, -Asp-Asp(OBzl)—OH, -Glu(NBzl$_2$)—OH, -Glu(NHBzl)—OH, -Asp(NBzl$_2$)—OH, -Asp(NHBzl)—OH, -Glu-NBzl$_2$, -Glu—NHBzl, -Asp-NBzl$_2$, -Asp—NHBzl, -Glu—NHCHPhCH$_2$Ph, -Asp—NHCHPhCH$_2$Ph, -Glu—NHCH$_2$CHPh$_2$, -Asp—NHCH$_2$CHPh$_2$, -Glu(NHCHPhCH$_2$Ph)—OH, -Asp(NHCHPhCH$_2$Ph)—OH -Glu(NHCH$_2$CHPh$_2$)—OH, -Asp(NHCH$_2$CHPh$_2$)—OH, -Glu(NHCH$_2$CH$_2$-Ind)—OH, -Asp(NHCH$_2$CH$_2$-Ind)—OH, -Glu—NHCH$_2$CH$_2$-Ind, -Asp—NHCH$_2$CH$_2$-Ind, -Trp—NH—Ind(OH), -Tyr-Iqu(OH), -(I)Tyr-Phe—OH, -Trp-Trp—OH, -Tyr(Bzl)-Phe—OH, -Tyr(Bzl)-Trp—OH, -(I)Tyr-Trp—OH, -(I)Try-Tyr—OH, -Trp-His—OH, -His-Trp—OH, -Tyr-His—OH, -His-Tyr—OH, -Phe-His—OH, -His-Phe—OH, -Phe-Trp—OH, -Phe-Tyr—OH and -Phe-Phe—OH.

27. The peptide as claimed in claim 1 wherein X is selected from the group consisting of -Tyr—OH, -Phe—OH, -Trp—OH, -Phg—OH, -Tyr-Phe—OH, -Tyr-Trp—OH, -Trp-Trp—OH, -(m-F)Tyr—OH, -(P-F)Phe—OH, -(m-F)Tyr-(pF)Phe—OPH, -(I)Tyr-Phe—OH, -Tyr(Bzl)-Phe—OH, -Trp(Bzl)-Phe—OH, -(I)Tyr-Trp—OH, -(I)Tyr-Tyr—OH, -Glu(OBzl)—OH, -Glu-OBzl, -Asp(OBzl)—OH, -Asp—Obzl, -Glu—NHCHPhCH$_2$Ph, -Glu—NHCH$_2$CHPh$_2$, -Asp—NHCHPhCH$_2$Ph, -Asp—NHCH$_2$CHPh$_2$, -Asp—NHCH$_2$CH$_2$—Ind, -Asp-(NHCH$_2$CH$_2$—Ind)—OH, -Glu-Asp—NHCH$_2$CH$_2$—Ind, -Glu-Asp(NHCH$_2$CH$_2$—Ind)-NBzl$_2$, -Asp-NBzl$_2$, -Trp—NH—Ind and -Trp-Iqu.

28. The peptide as claimed in claim 1 wherein n is 0.

29. The peptide as claimed in claim 1 wherein n is 0 and the —N(R$_5$)—(HCR$_6$)—(CH$_2$)n—CO— moiety is an α-amino acid residue selected from the group consisting of Ala, Val, Leu, Ile, Trp, Pya(2) and Pya(3).

30. The peptide as claimed in claim 1 wherein n is 2, 3 or 5.

31. The peptide as claimed in claim 1 wherein R$_1$ is a hexamethyleneimino group, R$_2$ is a hydrogen atom, R$_3$ is a C$_{1-6}$ alkyl group, R$_4$ is a indol-3-yl-C$_{1-6}$ alkyl group, R$_5$ is a hydrogen atom, R$_6$ is a C$_{1-6}$ alkyl group or a 5- or 6-membered aromatic heterocyclic group having 1 to 4 hetero atoms of O, S and N, m is 2, n is 0 and X is -Tyr-(D)-Phe—OH, -Tyr(I)-(D)Phe—OH or -Trp—NH—Ind—OH.

32. The peptide as claimed in claim 1 wherein R$_1$ is a hexamethyleneimino group, R$_2$ is a hydrogen atom, R$_3$ is a C$_{1-6}$ alkyl group, R$_4$ is a indol3-yl-C$_{1-6}$ alkyl group, R$_5$ is a hydrogen atom, R$_6$ is a C$_{1-6}$ alkyl group, m is 2, n is 0 and X is -Tyr-(D)Phe—OH.

33. Hexamethyleneimino—CO—Leu-(D)Trp-(D)Ala-βAla-Tyr-(D)Phe—OH, or a pharmaceutically acceptable salt thereof.

34. Hexamethyleneimino—CO—Leu-(D)Trp-(D)Ala-βAla-Tyr(I)-(D)Phe—OH, or a pharmaceutically acceptable salt thereof.

35. Hexamethyleneimino—CO—Leu-(D)Trp-(D)Ala-βAla-Trp—NH—Ind—OH, or a pharmaceutically acceptable salt thereof.

36. Hexamethyleneimino—CO-Leu-(D)Trp-(D)Ala-βAla-Tyr-(D)Phe—OH, or a pharmaceutically acceptable salt thereof.

37. A pharmaceutical composition containing the peptide of claim 1 or a pharmacologically acceptable salt thereof.

38. The pharmaceutical composition of claim 7 which is an endothelin receptor antagonist.

39. The pharmaceutical composition of claim 7 which is an endothelin receptor antagonist.

* * * * *